United States Patent [19]
Madden et al.

[11] Patent Number: 5,694,933
[45] Date of Patent: Dec. 9, 1997

[54] APPARATUS AND METHODS FOR DETERMINING SPATIAL COORDINATES OF RADIOLABELLED TISSUE USING GAMMA-RAYS AND ASSOCIATED CHARACTERISTIC X-RAYS

[75] Inventors: Norman Madden, Livermore; Richard Pehl, Berkley, both of Calif.; Robert G. Carroll, Largo, Fla.; Louis McKellar, Los Altos, Calif.

[73] Assignee: Care Wise Medical Products Corporation, Morgan Hill, Calif.

[21] Appl. No.: 430,589

[22] Filed: Apr. 28, 1995

[51] Int. Cl.⁶ .......................................................... A61B 5/05
[52] U.S. Cl. ................ 128/653.1; 128/659; 250/363.02; 250/363.1
[58] Field of Search .............................. 128/653.1, 659; 250/363.02, 363.1, 363.07; 364/413.24, 413.26; 600/1

[56] References Cited

U.S. PATENT DOCUMENTS

| | | | |
|---|---|---|---|
| 3,843,881 | 10/1974 | Barton, Jr. et al. | |
| 3,936,646 | 2/1976 | Jonker. | |
| 3,955,088 | 5/1976 | Muehllehner et al. | 250/367 |
| 4,150,289 | 4/1979 | Rosauer et al. | |
| 4,340,818 | 7/1982 | Barnes. | |
| 4,419,585 | 12/1983 | Strauss et al. | |
| 4,489,426 | 12/1984 | Grass et al. | |
| 4,671,256 | 6/1987 | Lemelson. | |
| 4,682,604 | 7/1987 | Fymat et al. | 128/659 |
| 4,782,840 | 11/1988 | Martin, Jr. et al. | 128/654 |
| 4,801,803 | 1/1989 | Denen et al. | |
| 4,868,856 | 9/1989 | Frith et al. | 378/86 |
| 4,873,632 | 10/1989 | Logan et al. | |
| 4,893,013 | 1/1990 | Denen et al. | 128/659 |

(List continued on next page.)

OTHER PUBLICATIONS

"The Clinical Use of Radioactive Phosphorous", in the Annals of Surgery, vol. 130, pp. 643–651 (1949).
"A Miniaturized Probe For Detecting Radioactivity at Thyroid Surgery", in Physics In Medicine and Biology, vol. 15, pp. 397–404 (1971).
"Single Photon Scatter Compensation By Photopeak Energy Distribution Analysis", IEEE Transactions on Medical Imaging, vol. 11, pp. 161–164, Jun., 1992.
"A CSI–Crystal Surgical Scintillation Probe", in Nucleonics, vol. 14, pp. 102–108 (Nov. 1956).

*Primary Examiner*—Brian L. Casler
*Attorney, Agent, or Firm*—Caesar, Rivise, Bernstein, Cohen & Pokotilow, Ltd.

[57] ABSTRACT

A system and method for diagnostic testing of structures within a body, e.g., organs within the body of a living being, which has been provided with a radioactive imaging agent, e.g., a radiotracer, to cause the structure to produce gamma rays, associated characteristic x rays, and a continuum of Compton-scattered photons. The system includes a radiation receiving device, e.g., a hand-held probe or camera, an associated signal processor, and an analyzer. The radiation receiving device is arranged to be located adjacent the body and the structure for receiving gamma rays and characteristic x rays emitted from the structure and for providing a processed electrical signal representative thereof. The processed electrical signal includes a first portion representing the characteristic x rays received and a second portion representing the gamma rays received. In a preferred embodiment of the invention the signal processor removes the signal corresponding to the Compton-scattered photons from the electrical signal in the region of the full-energy gamma ray and the characteristic x ray. The analyzer is arranged to selectively use the x-ray portion of said processed signal to provide near-field information about the structure, to selectively use both the x-ray and the gamma-ray portions of said processed signal to provide near-field and far-field information about the structure, and to selectively use the gamma-ray portion of said processed signal to provide extended field information about the structure.

93 Claims, 13 Drawing Sheets

U.S. PATENT DOCUMENTS

| | | |
|---|---|---|
| 4,949,365 | 8/1990 | Koike et al. . |
| 4,959,547 | 9/1990 | Carroll et al. . |
| 4,995,396 | 2/1991 | Inaba et al. .............................. 128/654 |
| 5,003,980 | 4/1991 | Loo et al. ............................ 128/653.1 |
| 5,036,210 | 7/1991 | Goodman . |
| 5,068,883 | 11/1991 | DeHaan et al. . |
| 5,148,040 | 9/1992 | Wise, Jr. et al. . |
| 5,165,410 | 11/1992 | Warne et al. ............................ 128/659 |
| 5,519,221 | 5/1996 | Weinberg .............................. 250/363.02 |

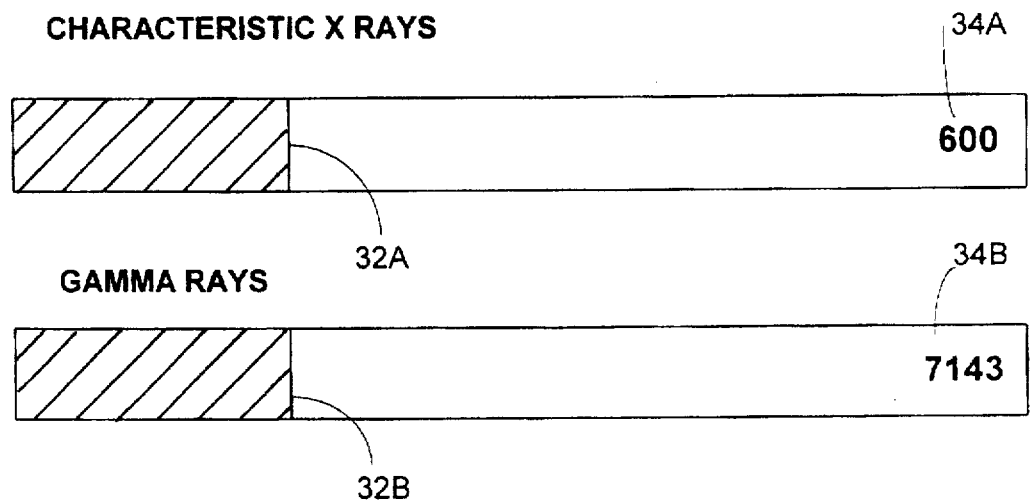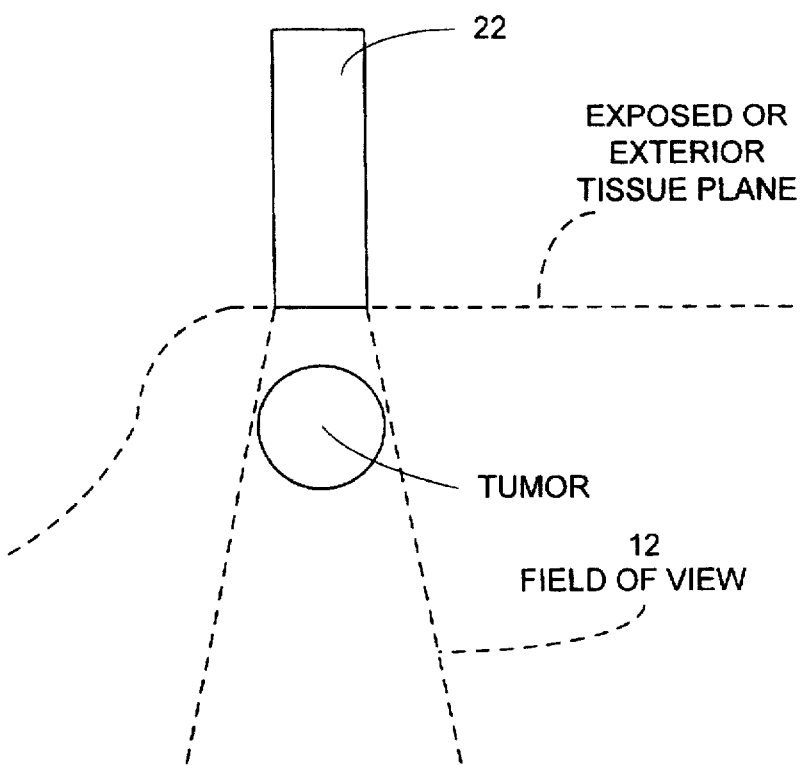
Fig. 3

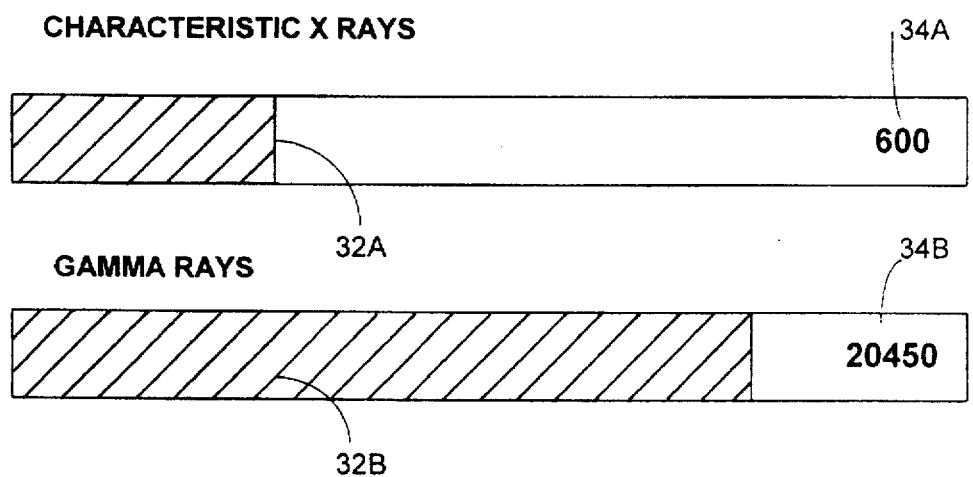
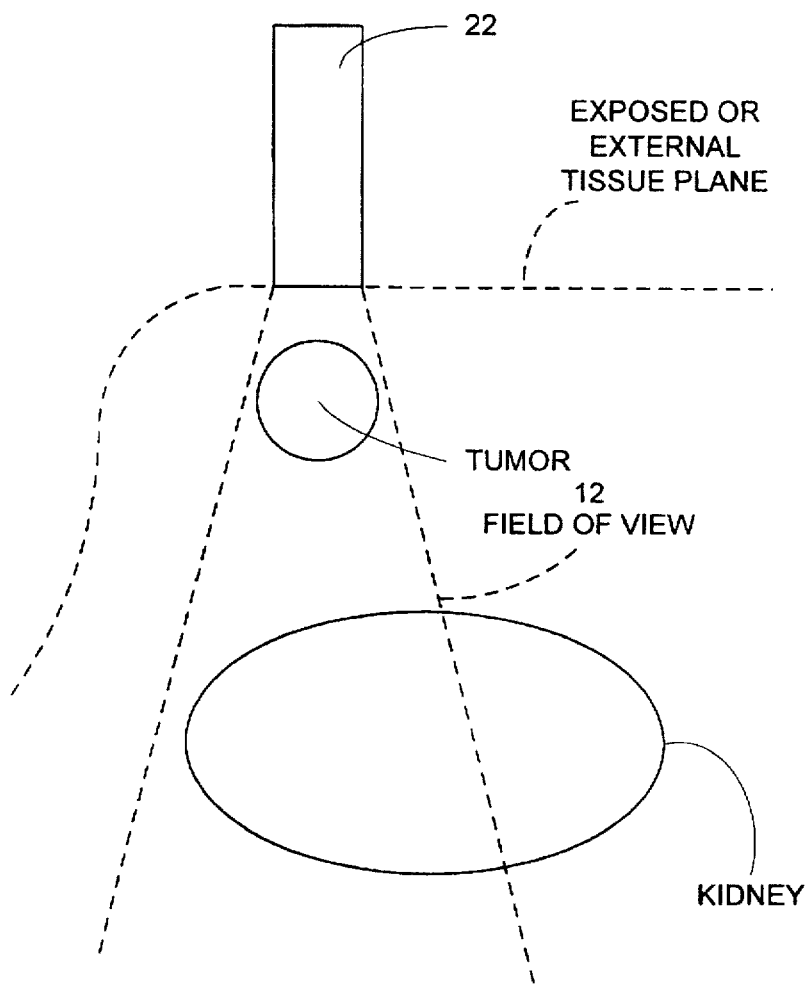
Fig. 4

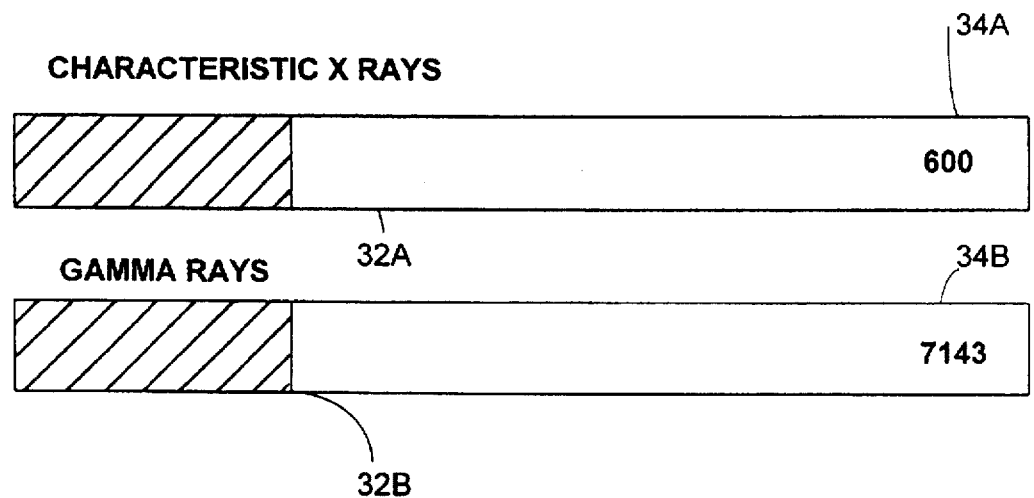
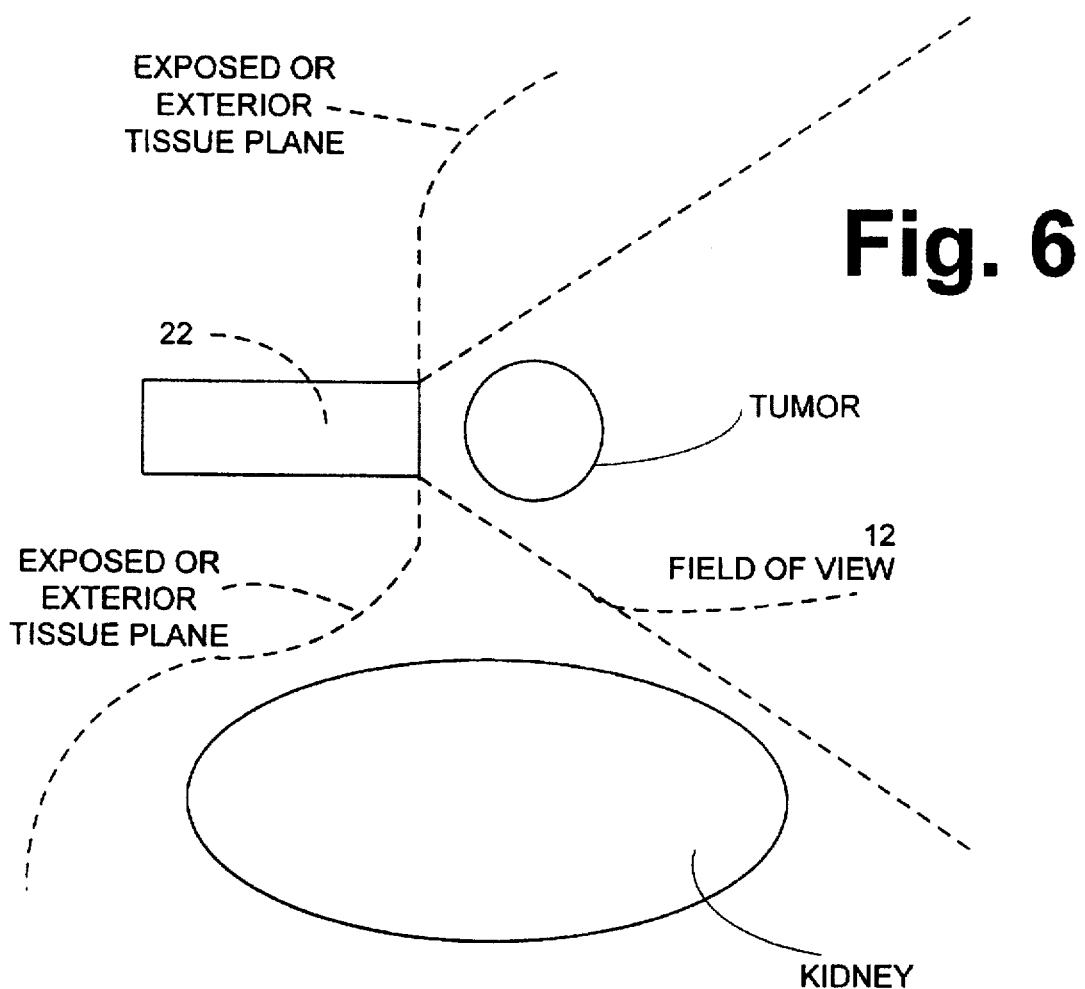
Fig. 6

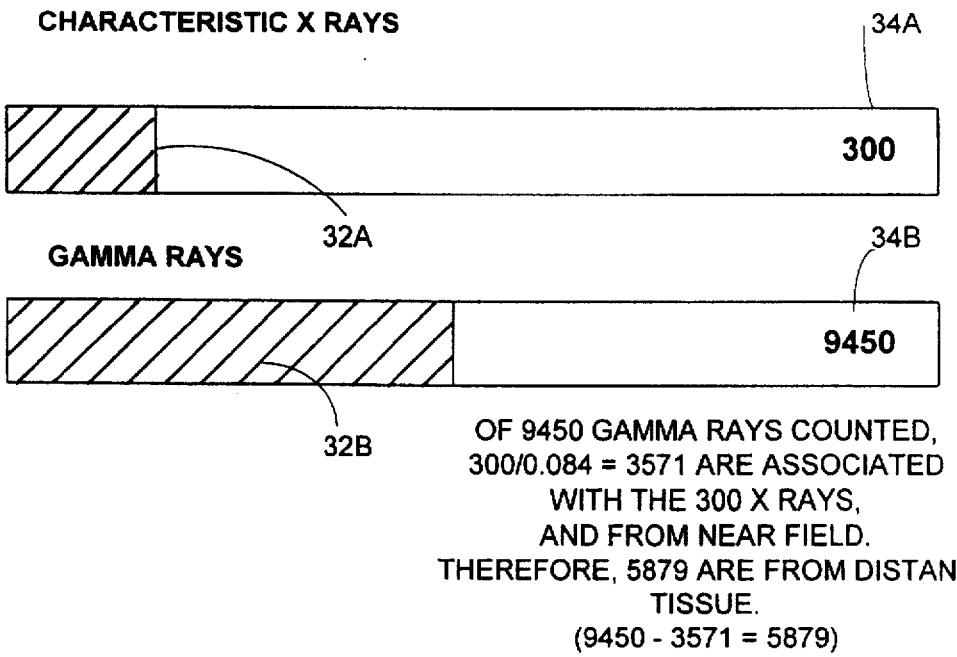
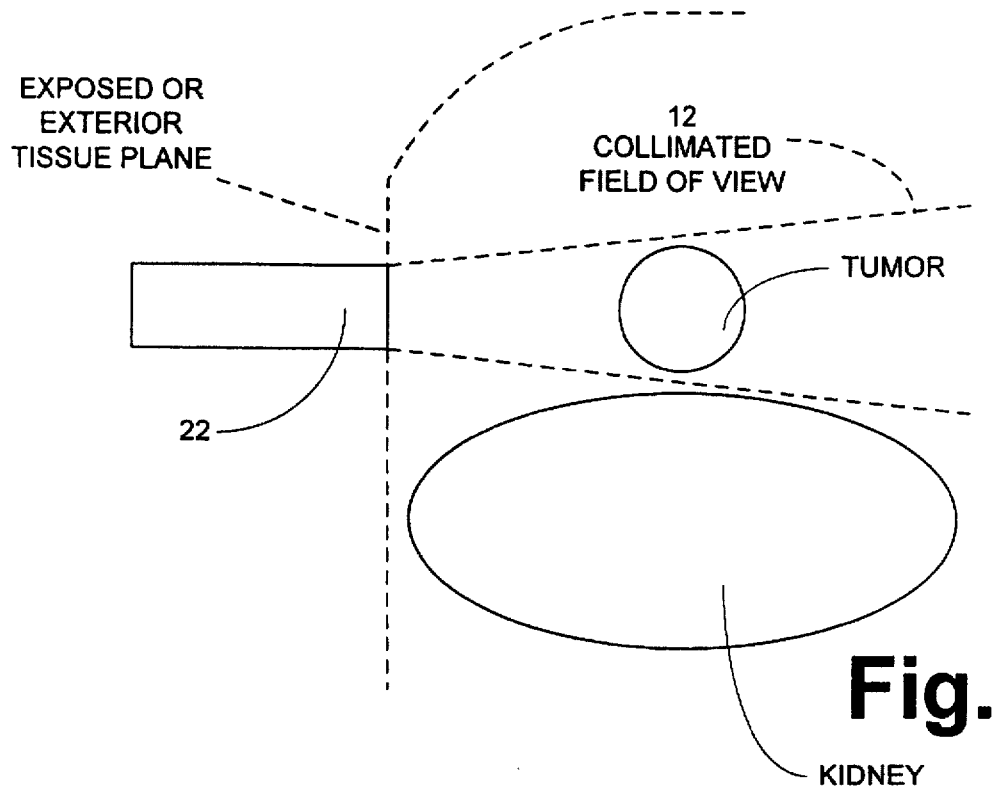
Fig. 9

APPARATUS AND METHODS FOR DETERMINING SPATIAL COORDINATES OF RADIOLABELLED TISSUE USING GAMMA-RAYS AND ASSOCIATED CHARACTERISTIC X-RAYS

BACKGROUND OF THE INVENTION

This invention relates generally to apparatus and methods for detecting radiation in order to determine the spatial coordinates of structures within a body, e.g. within the body of, or within a diagnostic tissue sample from, a living being, and for estimating the density of intervening tissue lying between the radiation detecting apparatus and said structures ("intervening tissue"). Specifically, this invention relates to a method and apparatus for utilizing a broad spectrum of photon radiation including x rays, gamma rays, and x rays in conjunction with gamma rays, for diagnostic procedures.

Examples of some specific apparatuses and methods to which this invention relates are: hand-held nuclear uptake probes for use in open surgical procedures, in endoscopic procedures, transcutaneously, in open and closed biopsy procedures, and on ex vivo tissue specimens, as well as nuclear medicine imaging cameras ("gamma cameras"), including those designed for operative use.

The use of radioactive pharmaceuticals known as radiotracers to tag tissue within a patient for affecting the localization and demarcation of this tissue by radiation detecting devices including operative nuclear uptake probes has been disclosed in the medical literature for at least forty years. In the diagnosis and/or treatment of certain diseases, e.g., cancer, substances are introduced into the body that recognize or identify diseased tissue, such as tumors, or other tissues of clinical interest (such as certain lymph nodes). Examples of such substances include Iodine 125, Iodine 131, Phosphorous 32, in appropriate solutions, which are themselves intrinsically radioactive. Other examples are materials such as monoclonal antibodies, peptides, and certain colloids, which have been labelled with radioactive isotopes. The combination of the tissue-recognizing or identifying substance and the radioactive isotope (or "radioisotope") is referred to collectively as a radiotracer; similarly, the radioisotope which can itself recognize tissue of interest (e.g. Iodine 125) is also referred to as a radiotracer.

When injected intravenously, the radiotracer circulates throughout the body. Once the radiotracer encounters the target tissue cells, the radiotracer will adhere to or be absorbed (i.e. "be taken up") by those cells in concentrated amounts. Locations where radiotracers are taken up in concentrated amounts by the targeted tissue cells of clinical interest are known as areas of "specific uptake." Often only a small percentage, e.g., from less than one to five percent, of the total radiotracer injected will actually be taken up at the site of specific uptake. The remainder of the injected radiotracer will circulate to other regions and tissues of the body that are of no clinical interest, e.g., non-cancerous tissue, including circulating blood, and healthy bone marrow, liver and kidneys. The radioisotope of the radiotracer undergoes radioactive decay; that is, over time, the radioisotope experiences spontaneous nuclear transitions resulting in the emission of radiation, which typically includes gamma-ray photons and x-ray photons.

The radiotracer circulates and interacts with tissue and organs located throughout the body, such that these photons are emitted in random directions from locations that are of no clinical interest as well as from locations of specific uptake. Under prior art methods in nuclear medicine, practitioners are interested in detecting and evaluating gamma-ray photons that are emitted from the locations of specific uptake, while seeking to eliminate from the evaluation all photons emitted from sources that are of no clinical interest, e.g. non-cancerous tissue, circulating blood, and disease-free bone marrow, liver, and kidneys.

The energies of the gamma-ray photons emitted by the radioisotopes are unique to each isotope. At the time of their creation, these gamma rays are termed "full energy" or "primary" gamma rays. For the emitted photon to have enough energy to exit the patent's body in sufficient quantities to be able to form an image in a gamma camera, its energy must be above about 60 keV. For radiotracers in common use, the gamma-ray energies may be as high as about 511 keV. As an example, when Technetium 99 m, an isotope often used in nuclear medicine, decays, 89% of the time a full-energy 140-keV gamma ray is emitted. Natural abundance ("abundance") or yield refers to the percentage of time that a decay or disintegration of the radioisotope nucleus results in production of the photon of interest, in this case the 140-keV full-energy gamma-ray photon. Indium 111, another commonly used radioisotope, emits 172-keV full-energy gamma rays, with an abundance of 89.6%, and 247-keV full-energy gamma rays, with an abundance of 93.9%.

These gamma-ray emitting radioisotopes also emit characteristic x rays. The characteristic x rays originate in the following way. When the nucleus undergoes radioactive decay, an electron is sometimes removed from one of the orbital shells, most often the inner orbital shell. An electron from one of the outer orbital shells promptly falls back to the inner shell to take the place of the ejected electron so that the atom returns to its ground state. This action results in the emission of a characteristic x ray. The emitted x ray is described as "characteristic" because its energy is characteristic of the specific element involved. Characteristic x-ray emissions from radioisotopes used in nuclear medicine are typically of low energies i.e., from about 15 to 30 keV. For example, the radioactive decay of Technetium 99 m results in Technetium characteristic x rays of about 19 keV, with an abundance of 7.5%, in addition to the 140 keV gamma ray previously discussed. The radioactive decay of Indium 111 results in Cadmium characteristic x-rays of approximately 24 keV, with an abundance of 83.5%.

The ratio of the number of full-energy gamma rays to the number of characteristic x rays emitted by each radioisotope is fixed and known, and reflected in the related abundance figures.

Under prior art methods in nuclear medicine, practitioners have typically utilized either the full-energy gamma rays alone in determining the location of cancerous or other tissues of interest in one instance, the combined signal from detection of both x rays and gamma rays together, without separately measuring and comparing the two signals, is being used. This is being done in the NEOPROBE device, made by Neoprobe Corporation of Columbus, Ohio. The NEOPROBE device detects both the 27-keV x rays and 35-keV gamma rays from Iodine 125.

There are several factors that make the evaluation of full-energy gamma-ray photons difficult. These factors have tended to make the detection and evaluation of the characteristic x rays even more difficult. Other than in the NEOPROBE device mentioned above, practitioners have seldom utilized the characteristic x rays and largely have not recognized the utility of the characteristic x ray in nuclear medicine. No practitioners have utilized the separate signals from characteristic x rays and the separate signals from gamma rays, and compared them to each other, in order to determine the spatial coordinates of tissue with nuclear uptake, or of the density of intervening tissue. Some of the problems associated with the use of both full-energy gamma rays and characteristic x rays, together and separately, to locate tissues of interest are discussed below.

Soft tissue in the human body is largely water, with small admixtures of light elements. Therefore soft tissue, blood, and most tumors have similar densities, approximately that of water. Bone is much denser, while lungs, because of their large air content, have effective densities much less than water. The probability of photons being absorbed as they move through matter is exponential. Gamma rays with energies from 60 to 500 keV usually travel relatively long distances before absorption in soft tissue (several hundred millimeters), whereas characteristic x rays of about 20 to 30 keV usually travel substantially shorter distances (30 millimeters or less). Consequently, these x rays cannot create images in gamma cameras because they are virtually all absorbed by fat, muscle, and skin.

Furthermore, as previously mentioned, in addition to being taken up in tissue of clinical importance, imaging radiotracers may also be taken up in tissues and body fluids, such as blood, that are not of clinical interest. In the instance of Indium-111 labeled cancer-seeking antibodies, for example, a twenty-gram tumor may have only one percent of the total injected radiopharmaceutical dose, whereas the liver may have thirty five percent of the injected dose, on a non-specific basis (i.e., with no cancer present in the liver). The number of detected full-energy gamma rays from said liver, as measured by a hand-held nuclear uptake probe, may be from ten to one hundred times greater than those from the tumor. Significant radiation activity may also persist in circulating blood and in disease-free bone marrow throughout the body. As another example, Technetium 99 m-labeled antibodies often show strong nonspecific uptake in the kidneys. This non-specific uptake in tissues which are not of clinical interest is an important source of background radiation.

The photons that lose energy and change direction due to the process known as Compton scattering represent additional background radiation. Compton scattering takes place when a photon interacts with an electron, and thereby loses energy and changes direction. The Compton scattering which results from the interaction of incident gamma photons with electrons of body tissues creates a virtual sea of scattered photons having energies ranging from slightly below the full-energy gamma-ray photons down to and below typical x ray energies ("the Compton continuum"). The directions, and thus the apparent points of origin of these Compton-scattered photons have only a limited relationship to the site from which the original, unscattered, full-energy gamma rays originated, and therefore have little relationship to the location of the tissue of interest.

The widespread distribution of radiotracers often encountered in tissues which are not of clinical interest described above, including the relatively high preferential uptake in certain organs, plus the additional radiation from Compton-scattered photons contributes to nonuniform and sometimes very intense levels of non-specific background radiation.

Under prior art methods, these marked variations in background radiation, including misleading signal from organs with no disease but high uptake, plus the abundant, almost randomly-directed Compton-scattered photons have seriously compromised the search for specifically labelled tissue with hand-held probes and with gamma cameras. Further, the Compton-scattered photons add background radiation and compete for processing time with signal corresponding to unscattered gamma rays and x rays.

There are additional drawbacks associated with prior art methods of detecting full-energy gamma ray photons. The attenuation by body tissues of full-energy gamma-rays from very small tumors located deep within the patient's body have resulted in an inability of gamma cameras to locate many such sites. This problem is made more severe because some tumors simply fail to take up enough radiotracer to be detected at a distance. Since 1949 operative nuclear uptake probes have been used by surgeons in an effort to overcome these drawbacks.

Prior art hand-held nuclear uptake probes can be classified into two categories, contact probes and extended-range probes. Contact probes have been used to detect radiation having a short range, such as electrons and positrons from beta decay, and relatively low energy photons (i.e., below 60 keV). Examples are the 27-keV x rays and 35-keV full-energy gamma rays of Iodine 125. These contact applications are characterized by significant reduction in the number of full-energy photons detected due to the absorption and/or scattering of the radiation that occurs in overlying or commingled tissue of only a few millimeters depth. Consequently, contact probes are limited to applications wherein the probe is essentially in contact with the radio-labeled tissue of interest. This limitation is an advantage in situations of modest specific tissue uptake coupled with high non-specific background radiation from underlying tissue, such as is the case with some radiolabeled monoclonal antibodies. Such contact probes share features of excellent localization when radiolabels are used that emit only lower energy photons with short ranges in tissue,as is the case with Iodine 125. However, gamma camera images cannot be obtained of tissues labeled with radiotracers that emit only short-ranged radiation, as mentioned earlier. Further, it is difficult to use such contact nuclear uptake probes to scan tissues for radiolabeled sites of unknown depth.

As reported in an article entitled "The Clinical Use Of Radioactive Phosphorous", in the Annals of Surgery, Vol. 130, pps. 643–651 (1949), by Selverstone, Sweet, and Robinson, those authors used a contact hand-held nuclear uptake probe to determine boundaries of resection in a glioblastoma multiforme. They used Phosphorus-32 which emits a beta particle. These were detected with a blunt needle Geiger-Mueller detector. In this instance signal-to-noise ratio was excellent because the normal brain has an intact blood brain barrier which excludes Phosphorus. The short range of about one millimeter of the Beta particle in tissue obviated background from bone marrow as well as from more distant sources. No use of characteristic x rays and gamma rays was made by Selverstone, et al.

The use of extended-range nuclear uptake probes was reported by Craig, Harris, et al, in an article entitled "A CSI—Crystal Surgical Scintillation Probe", in Nucleonics, Volume 14, pps. 102—108 (November 1956). In a case of post-operative residual tissue, tissues labelled with Iodine 131, which emits full-energy 364-keV gamma rays, were localized using a Cesium Iodide scintillation-crystal-based hand-held nuclear uptake probe. This probe used a light pipe to transmit the scintillation signal to a photomultiplier tube. The very high physiological concentration of Iodine 131 by the thyroid provided large numbers of detected photons while absence of other Iodine concentrations in the neck minimized background radiation. Shielding and collimation were used to minimize detection of background radiation from Iodine 131 in the gastric mucosa. In 1971, A. C. Morris, T. R. Barclay, A. Tanida, et al. reported on using a transistorized version of this CsI probe in an article entitled "A Miniaturized Probe For Detecting Radioactivity At Thyroid Surgery", in Physics In Medicine And Biology, Volume 15, pps. 397–404 (1971).

Under conditions of high uptake in the tissue of interest, rapid blood pool clearance, and low non-specific uptake, probe localization of radiolabelled tissues can be relatively easy. Current Technetium 99 m sulfur colloid lymph node mapping techniques for finding the sentinel node in melanoma and breast cancer approach this ideal. Imaging provides a map of the actual anatomic distribution of lymph node drainage patterns, while the probe readily finds small nodes deep in fat and other tissue.

Many radiotracers are far from ideal for probe use because of limited tumor-to-background contrast, abundant far-field non-specific uptake, and slow blood pool clearance relative to the physical half life of the radioisotope. Indium 111 labelled monoclonal antibodies, such as Oncoscint® marketed by Cytogen Corporation, has about 0.05% injected dose per gram of tumor. The signal from this low does competes with that from about 35% of the dose in the 1800 gram liver. As mentioned previously, this can result in full-energy gamma rays from said liver, as measured by a hand-held nuclear uptake probe, being from ten to one hundred times greater than those from the tumor.

There is also significant uptake in the bone marrow, and in circulating blood. On Nuclear Medicine scans, tumor is about the same density as imaged large blood vessels, which are commonly immediately adjacent to tumor involved lymph nodes.

Neoprobe Corporation provides a device for a method wherein a tumor-seeking monoclonal antibody is tagged with the radioactive isotope Iodine-125 and injected into the body to determine the location of cancerous tissue. See U.S. Pat. Nos. 4,782,840, 4,801,803, and 4,893,013. Iodine 125, whose half-life is 60 days emits a full-energy 35-key gamma-ray at the low energy of 35 keV and a 27-keV characteristic x-ray. These photons are detected in a single broad energy window by the practitioner during surgical exploration with the use of a hand-held contact nuclear uptake probe. The relatively long half-life of 60 days (i.e., long compared to that of many other imaging nuclear medicine radioisotopes) allows the practitioner to wait until much of the radiotracer has been biologically cleared from the blood pool and the background radiation has been much reduced. However, this process reportedly takes about three weeks, and thus causes a corresponding delay of surgery. This delay is considered by some practitioners to be a disadvantage. In addition, the low energy photons can not be used for preoperative imaging by gamma cameras. If a Technetium-99 m bone scan or Indium-111 white cell scan is done close to the scheduled date of surgery, background radiation arising from Compton scattering of full-energy gamma rays emitted by Technetium or Indium can make Iodine-125 localization extremely difficult. The NEOPROBE device uses a single energy "window" or band wide enough to include both the 27-keV characteristic x ray and the full-energy 35 keV gamma ray, and thus cannot distinguish between these two photons.

Other techniques employed with hand-held surgical nuclear uptake probes to deal with background radiation have included: control measurements of uptake of adjacent tissues, using identical probe angular orientation; aiming the probe consistently away from all organs with high non-specific uptake, with extended-field probes; use of a hand-held or hand-placed radiation blocking plate, with extended-field probes; use of a "window" which limits the photons measured by the radiation-detecting system to those of energies close to that of the full-energy gamma-ray peak; and the use of collimation appropriate to the size and also the depth of the lesion.

Operative nuclear uptake probes augmented by radiation blocking plates and selectable collimation are the subjects of U.S. Pat. Nos. 5,148,040, 4,959,547, and 5,036,210.

While each of these techniques has markedly reduced the problems caused by non-specific background radiation, there are circumstances in which one or more of these techniques can not be easily employed, the methods are sometimes time-consuming, or a high degree of familiarity and specific experience is required of the practitioner.

For example, extended-field probes are challenged by applications involving Indium-111 labelled antibodies. About 35 percent of the activity can be from non-specific liver uptake. Tumor activity is often diffusely present throughout the bone marrow, and the tumor activity per gram is often similar to that found in circulating blood. Despite techniques such as aiming the probe to avoid sites of known high non-specific uptake, use of selectable collimation, and use of a radiation-blocking plate where anatomically possible, the acquisition of good intraoperative skills by the practitioner can be very time-consuming.

Contact probes, on the other hand, are severely limited by attenuation by overlying tissue of only a few centimeters thickness. The tissue of interest, such as a tumor, must be almost completely exposed and essentially in contact with the probe in order for the probe to detect the uptake. Consequently, it is difficult to use contact nuclear uptake probes to scan tissues for radiolabelled sites of unknown depth, or, for example, to explore for retroperitoneal nodes during colorectal procedures without surgically penetrating the peritoneum. Gamma camera images cannot be obtained using many of the radioisotopes used with contact probes, such as Iodine-125.

Compton-scatter correction for gamma camera imaging has been discussed in various articles. See for example, K. W. Logan and W. D. McFarland, "Single Photon Scatter Compensation By Photopeak Energy Distribution Analysis", IEEE Transactions on Medical Imaging, Vol. 11, pps. 161–164, June 1992. U.S. Pat. No. 4,873,632 (Logan et al.) discloses a system utilizing filtering to reduce background radiation introduced by Compton-scatter in imaging by means of a gamma camera.

U.S. Pat. No. 3,843,881 (Barton) discloses a method for detecting the presence of metals in subterranean formations. Under Barton, a formation is irradiated with high energy electromagnetic radiation from a suitable source, such as radioactive material. Characteristic x rays are emitted from the metals as the result of being irradiated. These x rays are detected and measured to provide information regarding the presence and type of metal ore in the formation. Barton does not disclose the measuring and comparing of the gamma ray to a characteristic x ray to determine lateral location and depth of radiolabelled objects, or depth of intervening material. Further, Barton does not make use of the display of gamma-ray or x-ray photons stripped of the display of radiation from Compton-scattered photons.

U.S. Pat. No. 4,949,365 (Koike) describes an apparatus for measuring the density of objects such as bones, by transmitting gamma rays having different energy levels. Koike does not make use of characteristic x rays and/or full-energy gamma rays for the measuring spatial coordinates. Further, Koike does not make use of the display of gamma-ray or x-ray peaks stripped of the display of radiation from Compton-scattered photons.

U.S. Pat. No. 3,936,646 (Jonker) describes a focusing collimator kit with multiple stackable components for isotope imaging. This patent does not disclose the use of combined characteristic x rays and gamma rays in the determination of spatial coordinates of the tissue detected, or of the density of intervening tissue. Further, Jonker does not make use of the display of gamma-ray or x-ray peaks stripped of the display of radiation from Compton-scattered photons.

U.S. Pat. No. 4,150,289 (Rosauer) describes a gamma-ray inspection system for measuring the wall thickness of a tubular product, and in particular an associated calibration block. This patent does not disclose the combined use of characteristic x rays and gamma rays in the determination of spatial coordinates of the material detected, or of the density of intervening material. Further, Rosauer does not make use of the display of gamma-ray or x-ray peaks stripped of the display of radiation from Compton-scattered photons.

U.S. Pat. No. 4,340,818 (Barnes) describes a scanning grid apparatus used in x-ray radiology that provides improved transmissivity of full-energy x rays passing through the subject while providing reduced scatter radiation penetration. This patent does not disclose the combined use of both characteristic x rays and full-energy gamma rays in the determination of spatial coordinates of the tissue detected, or of the density of intervening material. Further, Barnes does not make use of the display of radiation from Compton-scattered photons.

U.S. Pat. No. 4,419,585 (Strauss) describes a variable angle radiation collimator used in a gamma camera system for radiological examination of human subjects. The collimator proves collimation of gamma rays so as to transmit radiation in a predetermined orientation. This patent does not disclose the combined use of both characteristic x rays and full-energy gamma rays in the determination of spatial coordinates of the tissue detected, or of the density of intervening tissue. Further, Strauss does not make use of the display of gamma-ray or x-ray peaks stripped of the display of radiation from Compton-scattered photons.

U.S. Pat. No. 4,489,426 (Grass) describes a collimator for regulating the shape and size of the pattern of radiation projected on a radiation detector from a radiation source, particularly for regulating the beam of radiation in a medical diagnostic x-ray machine. This patent does not disclose the combined use of both characteristic x rays and full-energy gamma rays in the determination of spatial coordinates of the tissue detected, or of the density of intervening tissue. Further, Grass does not make use of the display of gamma-ray or x-ray peaks stripped of the display of radiation from Compton-scattered photons.

U.S. Pat. No. 5,068,883 (DeHaan) describes a contraband detection system employing two different sources of low-energy gamma rays, and a means of detecting backscatter from inspected objects. Depending upon the composition of the target volume, a portion of the gamma rays are backscattered and returned to the hand-held device. By quantitatively sensing these backscattered gamma rays, a rough qualitative determination can be made as to the density composition of the target volume. From such density information, reasonable inferences may be drawn as to whether the target volume includes certain types of contraband material. This patent does not disclose the combined use of both characteristic x rays and gamma rays in the determination of spatial coordinates of the material detected. Further, DeHaan does not make use of the display of gamma-ray or x-ray peaks stripped of the display of radiation from Compton-scattered photons.

Therefore, for the foregoing reasons, the prior art methods and devices used in nuclear medicine suffer from one or several drawbacks. Further, many of the prior art methods and devices relating to the use of radioactive isotopes do not disclose the use of both characteristic x rays and gamma rays, separately and/or simultaneously, in the determination of spatial coordinates of the tissue detected, or of the density of intervening tissue. Nor do they make use of the display of gamma-ray or x-ray peaks stripped of the display of radiation from Compton-scattered photons.

OBJECTS OF THE INVENTION

Accordingly, it is a general object of this invention to provide an apparatus and methods of use which overcome the disadvantages of the prior art.

It is a further object of this invention to provide apparatus and methods for providing useful information for determining the location of radiolabelled material, such as cancerous tissue.

It is a further object of this invention to provide apparatus and methods for localizing radiolabelled material, such as suspected cancerous tissue or certain lymph nodes, within the body of a living being.

It is a further object of this invention to provide apparatus and methods for detecting characteristic x-ray photons and full-energy gamma-ray photons by a detector and utilizing them in combination to provide information for determining the location of radiolabelled materials, with respect to a reference point.

It is a further object of this invention to provide apparatus and methods for detecting characteristic x-ray photons and full-energy gamma-ray photons and utilizing them in combination to localize radiolabelled materials within the body of a living being.

It is a further object of this invention to provide an apparatus and methods for detecting characteristic x-ray photons and full-energy gamma-ray photons by a detector and utilizing them in combination to provide information regarding the density of tissue intervening between radiolabelled materials and the detector.

It is a further object of this invention to provide apparatus and methods for detecting characteristic x-ray photons and full-energy gamma ray photons utilizing them in combination to provide visual and/or audible signals to aid in localizing radiolabelled materials within the body of a living being.

It is a further object of the present invention to provide an apparatus and methods for detecting characteristic x-ray photons and full-energy gamma ray photons from radiolabelled materials within the body of a living being, while minimizing the effects of Compton scattered photons or other background radiation.

SUMMARY OF THE INVENTION

These and other objects of this invention are achieved by providing a system and methods for determining the location of a mass of radiolabelled tissue within the body of, or within a diagnostic tissue sample from, a living being, with respect to a reference point, the tissue being previously tagged with at least one radiolabelled tracer producing gamma-ray photons, characteristic x-ray photons, and an associated continuum of Compton-scattered photons arising from interaction of said photons with tissue. The system comprises radiation detecting means, signal processing means and signal analyzing means.

The radiation detecting means, e.g., a hand-holdable surgical nuclear uptake probe, a percutaneous biopsy probe, an endoscopic probe, or a gamma-camera, etc., is positionable to a location adjacent the radiolabelled tissue for detecting the photons emitted thereby and for providing an electrical signal representative of the received photons. The radiation detecting means establishes the reference point.

In those instances wherein the radiation detecting means is one of the types of probes referred to above, the reference point is the point on the external or exposed tissue place directly beneath the tip of said probe, along the axis of said probe. In those instances wherein the radiation detecting means is a gamma camera, the reference point may be the point on the external or exposed tissue plane viewed by said gamma camera at which the central axis of said camera's detector array (perpendicular to the plane of said array) intersects said tissue plane. In general, the position of the radiation detecting means relative to said tissue plane and observed body of tissue can be used to establish the reference point.

The signal processing means utilizes the electrical signal from the radiation detecting means to produce a processed electrical signal representative of the number of photons detected as a function of their energies, as is generally done in energetic photon spectroscopy. The processed electrical signal (typically displayed as a histogram or spectrum) includes a first portion representing the characteristic x-ray photons received and a second portion representing the gamma-ray photons received. These first and second portions of the signal, when said signal is displayed as a histogram, are typically displayed as peaks, which are portions representing higher concentrations of photons of a given energy or energies than is represented in said histogram for energies slightly higher, and slightly lower, than those represented in said portions or peaks. Note that the terms "first portion" and "second portion" are descriptive titles of portions of said signal, and do not refer to the relative energies of photons which correspond to said portions. The energies of photons represented by the first portion may be either lower, or higher, than the energies of photons represented by the second portion; however, the energy of a characteristic x ray will usually be lower than that of the full-energy gamma ray of interest. Note also that for some radioisotopes, such as Indium 111 which has two full-energy gamma rays, and for cases in which more than one radioisotope may be employed, there may be a plurality of either first portions or second portions.

The analyzing means is arranged for analyzing at least a selected one of the first and second portions of the processed signal to establish the location of the mass of radiolabelled tissue with respect to the reference point.

In accordance with one aspect of the invention the analyzer is arranged to selectively utilize only the signal that corresponds to the characteristic x-ray peak; or to utilize both the signal that corresponds to the characteristic x-ray peak and the signal that corresponds to the full-energy gamma-ray peak; or to utilize only the signal that corresponds to the full-energy gamma-ray peak of the processed signal: in order to provide near-field; or very-near-field, intermediate-field, and/or far-field; or extended-field information, respectively, about the radiolabelled tissue. As used herein, "near field" refers to radiation originating from tissue lying at shallow depths, from which characteristic x rays may be detected; "far field" refers to gamma radiation which originates from tissues lying at depths greater than that from which emitted characteristic x rays can be detected; and "extended field" refers to detected gamma radiation of energies sufficient to have penetrated any depth of tissue in the body of interest. The near field may be subdivided into one or more "very-near fields" and one or more "intermediate fields," either by manipulating the relative data on the numbers of detected photons of at least one characteristic x-ray energy and of at least one gamma-ray energy, or by comparing the data from two or more spectral line shape measurements of two or more different photon peaks, and accordingly subdividing the depth of tissue from which the near field radiation is emitted.

In accordance with another aspect of the invention the system includes means to ensure that the processed signal represents only a much reduced contribution from Compton-scattered photons.

In accordance with yet another aspect of the invention the system includes ratio calculation means to which the processed electrical signal is provided, and subtraction calculation means. The ratio calculation means is arranged to utilize plural predetermined reference ratios, each of which is the ratio of the full-energy gamma-ray photons and the characteristic x-ray photons emitted from at least one radiolabelled tracer after passing a predetermined distance through a predetermined type of material, e.g., body tissue, bone, etc., and to compare said selected predetermined reference ratios to a ratio it calculates. In particular, the ratio calculation means utilizes the processed signal to provide a calculated ratio representing the ratio of the number of characteristic x-ray photons making up the first peak to the number of full-energy gamma-ray photons making up the second peak. The calculated ratio is compared to at least one of the predetermined reference ratios. The subtraction calculation means is provided for subtracting the full-energy gamma-ray photons corresponding to the characteristic x-ray photons of the first peak from the total full-energy gamma-ray photons of the second peak.

In accordance with yet another aspect of the invention the system includes spectral line shape analyzing means for analyzing the shape of at least one of the peaks to provide an indication of the amount of tissue or its density intervening between the radiolabelled tissue and the radiation detecting means. In order to use spectral line shape analyzing means to determine the amount of tissue, tissue density must be separately known, and to determine the density of tissue, the amount or thickness of intervening tissue must be separately known.

DESCRIPTION OF THE DRAWINGS

Other objects and many attendant features of this invention will become readily appreciated as the same becomes better understood by reference to the following detailed description when considered in connection with the accompanying drawings wherein:

FIG. 3 is an illustration of a portion of the system shown in FIGS. 1 and 2 being used to determine the location of a radiolabelled tumor in the near-field in accordance with one aspect of the method of this invention;

FIG. 4 is an illustration, like that of FIG. 3, but showing a portion of the system of FIGS. 1 and 2 at an initial step of being used to determine the location of a radiolabelled tumor located substantially in front of a kidney in accordance with one aspect of the method of this invention;

FIG. 6 is an illustration, like that of FIG. 5, but showing the system being used in yet a later step of determining the location of the radiolabelled tumor of FIG. 4;

FIG. 9 is an illustration, like that of FIG. 8, but showing the system being used in yet a later step of determining the location of the radiolabelled tumor of FIG. 7;

DETAILED DESCRIPTION OF THE PREFERRED EMBODIMENTS

Figure 1:
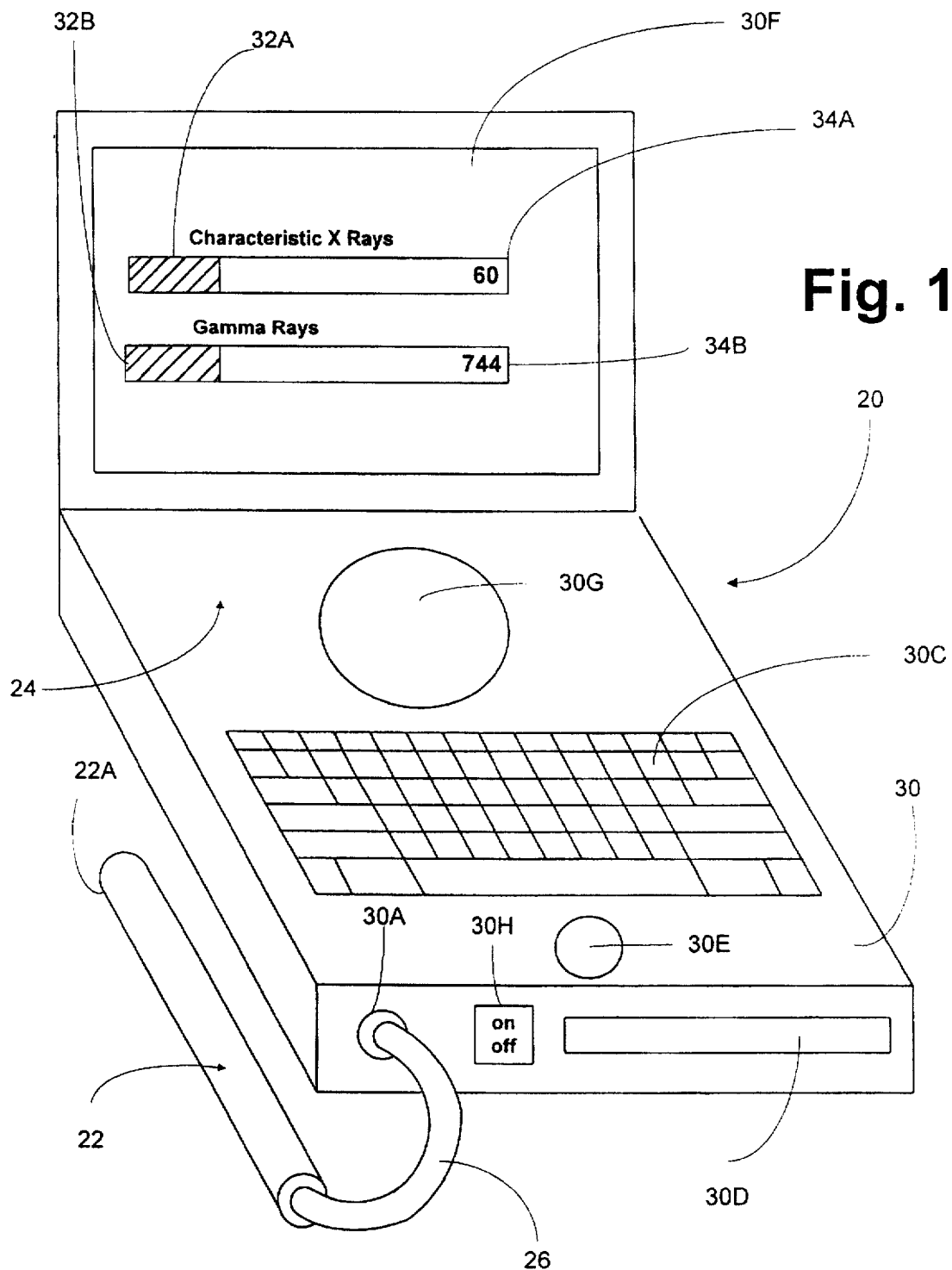
FIG. 1 is an isometric view of one embodiment of the system of present invention.

Referring now to various figures of the drawing where like reference numerals refer to like parts, in FIG. 1 there is shown generally at 20 a system for localizing radioactively tagged material, constructed in accordance with the present invention. In accordance with one preferred aspect of this invention the system is arranged to determine the nuclear uptake of radiolabelled tissue, e.g., a tumor lesion, or lymph node, within the body of, or within a diagnostic tissue sample from, a living being, and to provide information to the practitioner or user, e.g., a surgeon, regarding the location of the tumor, with respect to some predetermined reference point. In particular, the system is arranged to provide the practitioner with information to determine the center of the closest surface of the tumor, e.g., its "x" and "y" coordinates, as well as the distance or depth of that surface, e.g., the "z" coordinate, with respect to a predetermined reference point. The system also provides the practitioner with information regarding the density and/or amount of the intervening tissue lying between the radiolabelled tissue and the predetermined reference point.

This is accomplished by making use of the following behavior of photons as they travel through a substance, such as human tissue: the higher the energy of a photon, the further that photon is likely to travel through tissue of a given density and atomic number before it is scattered or absorbed; the greater the density and the greater the atomic number of the substance, the shorter the distance that a photon of a given energy is likely to travel before being scattered or absorbed; and in the instance of x rays and gamma rays, the greater the density and the greater the atomic number of the substance or the further the distance that the corresponding x rays or gamma rays travel, the greater the probability that the corresponding peak line shape will be asymmetrical. These behaviors depend upon the energy of the photon involved, not whether that photon is an x-ray photon or a gamma-ray photon.

Decisions made by the practitioner using said radiation detecting means regarding the presence or absence of clinically meaningful nuclear uptake in tissue must be based upon statistically significant data. The number of photons detected from sites of clinically meaningful uptake must be sufficiently abundant, relative to sites without meaningful uptake, such that the comparison of said numbers allows for sound statistical treatment which will provide the appropriate level of confidence to the practitioner. Accordingly, the time periods used for measurements of detected photons, and the amounts of radiotracer injected into the patient must be such to allow for sufficiently abundant photons to be emitted and detected from said sites of meaningful uptake, for the disease state or states of interest.

As will be appreciated by those skilled in the art from the discussion to follow, technological advancements that enable the subject invention to substantially overcome the previously mentioned drawbacks associated with prior art radiation imaging techniques have now been developed. For example, improved tumor detection can be achieved by placing a hand-held nuclear uptake probe or detector within the body during surgery, in close proximity to tissues of interest, thereby reducing the thickness of intervening tissues, in order to detect and evaluate radioactive emissions including gamma-ray photons and characteristic x-ray photons. Moreover, nuclear uptake probe systems that allow the practitioner to electronically select and view only photons within a specific range of energies are available. In addition, multi-channel analyzers have long been available to display meaningful peaks, corresponding to gamma ray and characteristic x-ray photon counts, arising from the continuum produced by Compton-scattered photons. All of the foregoing have contributed to the making of the subject invention, whose basis is the utilization of the characteristic x rays together with the "full-energy" or "primary" gamma rays of the radiolabeled tracer such that the number of detected x rays and the number of detected gamma rays can be used separately, and can be compared, to provide information to the practitioner regarding the location of tissue with nuclear uptake, including information on the depth of said tissue beneath the exposed or exterior tissue plane, and also information on the density of intervening tissue. The characteristic x rays have heretofore been usually undetected, or, if detected have usually been ignored due to the fact that they are of low energies and sometimes of low abundance so that when commingled with the relatively intense Compton-scattered photons, their signals are very difficult to extract.

By utilizing an optional aspect of this invention, the counts or events associated with detected Compton-scattered photons can be stripped away and eliminated by numerical fitting techniques, leaving only the characteristic x-ray and the full-energy gamma-ray peaks(s) for evaluation. As will be discussed later, software is commercially available to facilitate this process. Alternatively, or in addition, collimation can be utilized for restriction of field of view to reduce signals from unwanted Compton-scattered photons and other extended field background radiation.

Before describing the system 20, a brief description of the manner in which the tumor will have been tagged with a radiolabelled tracer will now be given. In particular, the patient is injected with a selected radiotracer 8, which may be monoclonal antibodies or other disease specific or anatomically or physiologically specific agents, labeled with one or more radioisotopes. Sufficient time is allowed for the radiotracer to circulate throughout the body and adhere to or be absorbed at the particular site-of-interest, e.g., cancerous tissue cells or tumors. As previously stated, often only a small percentage, e.g., one-half to five percent, of the radiotracer will actually be absorbed by or adhere to the organ or tissue that is of clinical interest and intended for examination, i.e., the site of "specific uptake". A much larger portion of the injected radiotracer often circulates to other areas of the body and interacts with body tissue and organs that may not be of clinical interest, such as non-cancerous tissue, circulating blood, bone marrow, extracellular fluid, the liver, and kidneys. Therefore, after circulating through the patient's body over a period of time, the radiotracer will concentrate at sites of specific uptake and will reside in dilute to high concentrations in some non-cancerous tissues, organs, extracellular fluid, and blood. High to very high concentrations of such "non-specific" uptake may be found, for example, in liver, with many Indium-111 labeled antibodies, and in kidneys with many Technetium-99 m labeled antibodies, as discussed earlier.

A radioisotope that is highly suitable as a radiolabel, to be part of a radiotracer to be injected into the human body in accordance with this invention, is Technetium 99 m, which emits full-energy gamma rays of 140 keV and characteristic x rays of approximately 19 keV. Examples of additional radioisotopes that may be employed in accordance with this invention include Indium 111 which emits full-energy gamma rays of approximately 247 keV and 172 keV and characteristic x rays of approximately 24 keV, and Iodine 123 which emits full-energy gamma rays of approximately 159 keV and Tellurium characteristic x rays of approximately 27 keV. Iodine 125 which emits full-energy gamma rays of 35 keV and Tellurium characteristic x rays of 27 keV may also be used, generally for tissues at depths not exceeding three centimeters.

Figure 2:
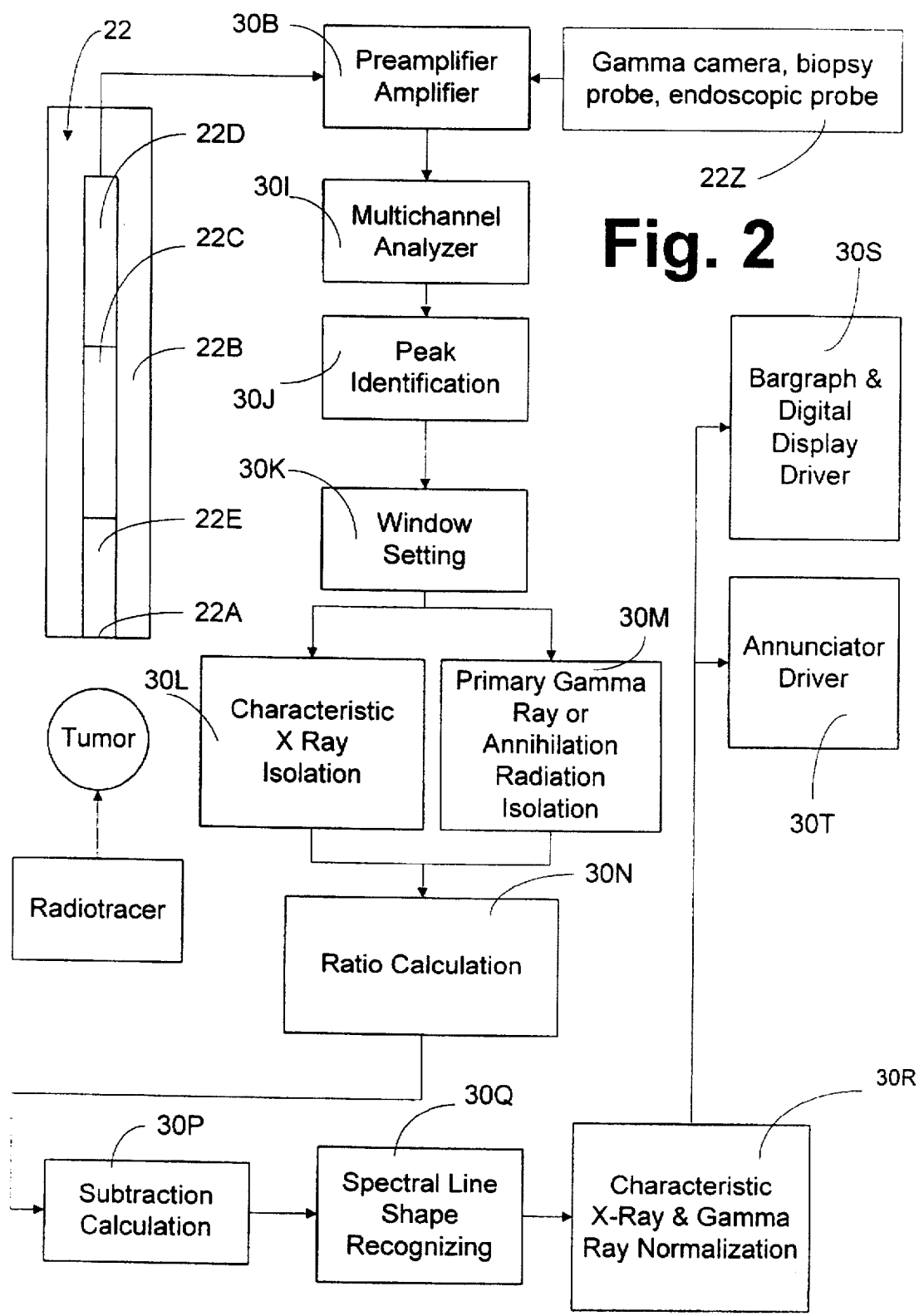
FIG. 2 is a block diagram showing the components making up the system of FIG. 1.

The system basically comprises a hand-held nuclear uptake probe 22 (or other radiation detector) and an electronic instrument 24 for processing signals from the probe. In accordance with one preferred embodiment of this invention, the probe is a small hand-held device, like that provided by Care Wise Medical Products Corporation of Morgan Hill, Calif., the assignee of this invention, under the trademark C-Trak®. The probe 22 is best seen in FIG. 2 and basically comprises a body member 22B formed of a radiation blocking material and having a hollow interior in which a radiation detector, e.g., a scintillation crystal 22C and an associated photomultiplier 22D are located. The front end or nose 22A of the probe defines a window or opening through which photons are received to hit the scintillation crystal 22C. Typically, the scintillation crystal 22C is comprised of either Sodium Iodide doped with Thallium, or Cesium Iodide doped with Sodium or Thallium.

The probe 22 is arranged to be held by the surgeon and located closely adjacent the site of the suspected tumor. If desired, the probe may be inserted through a natural body orifice, through a surgical wound or percutaneous incision or puncture to facilitate its placement. When placed within the proximity of the suspected tumor, the probe detects photons emitted or scattered from tissue lying within the probe's "field-of-view" 12. This field-of-view, as represented by the phantom lines in FIGS. 3–11, is sometimes called the "solid angle of acceptance", and is established by the size, depth, shape and location of the probe's window or opening with respect to its crystal 22C, and the size and shape of the crystal. The field of view can be described as a volume, typically conical or cylindrical in general shape, extending indefinitely into the space that is "viewed" by the detector through its window.

In accordance with a preferred aspect of this invention the probe 22 includes a collimator 22E located at the probe's window to establish the probe's field of view. The collimator 22E may be fixed or variable, as desired. In either case the desired acceptance angle of the field-of-view can be established. This feature may expedite the tumor localization procedure, as will be described later. It should be pointed out that, while a collimator may be desirable for some applications, it may be unnecessary for others. Thus, the use of a collimator, fixed or variable, is optional.

The probe 22 includes a output cable 26 coupled to the output of the photomultiplier. The cable includes a connector at its end which is arranged to be connected to an input connector 30A of the instrument 24 to provide electrical signals in the form of charge pulses in response to the receipt of photons by the probe. In particular, as photons are received by the probe they hit the scintillation crystal 22C, which causes the crystal to give off flashes of light or "scintillations" whose intensity is proportional to the energy of the photons received. The light flashes are intercepted by the photo cathode forming the front of the photomultiplier wherein electrons are released to provide electrical pulses which are proportional to the energy of the photons detected, with the number of pulses being proportional to the number of photons received. The resulting electrical signal is provided by the cable 26 to preamplifier and associated amplifier circuitry 30B (FIG. 2) which will be described later. The circuitry 30B forms a part of the instrument 24, but may be a separate component interconnected between the output of the probe and the input of the instrument 24. It is in the instrument 24 that the signal representative of the radiation detected by the probe 22 is processed and utilized in accordance with the present invention.

In an alternative embodiment of this invention, the detector used in the probe 22 is of a high resolution semiconductor design capable of directly converting detected radiation into electrical signals. In examples of such alternative embodiments the detector may be comprised of Cadmium Zinc Telluride, Germanium, or Silicon.

Another alternative embodiment of a probe for use in the system of this invention may have more than one detector, such as a probe with two independent detectors or independent segments of a detector, each of which is intended to monitor radiation from a specific kind or category of sites or of a specific energy or range of energies.

It should be pointed out that other radiation detecting means can be used with the system of this invention in lieu of the hand-held probe 22 described above. In this regard a conventional gamma camera, biopsy probe, endoscopic probe, or some other detector or operative camera can be utilized to detect the radiation emanating from the material to be localized.

When the probe 22 is located at some operative position with respect to the patient's body, the probe will detect an immense amount of photon emissions within its field-of-view. This includes full-energy gamma-ray and characteristic x-ray photons and Compton-scattered photons. These photons can originate from areas of no clinical interest and from sites of specific uptake, which are of clinical interest.

The instrument 24 provides a means for separating and displaying information obtained from the detection of photons of any specific energy or range of energies from that obtained from the detection of the other photons within the field of view, and also for further evaluation of this information based on relationships between the numbers of photons of different energies, such as those of the characteristic x rays and the full-energy gamma rays of a specific radioisotope (or radioisotopes), and also for further evaluation based on the effects of the passage of such photons through tissue. In particular, as will be described in detail later, the system of this invention provides the surgeon with a means for selectively monitoring only those photons of interest in clinical evaluation and to estimate the depth of tissue from which these photons originate, in order to determine the lateral location, e.g., X and Y coordinates, and the distance or depth location, e.g., Z coordinate, of the site of specific uptake, i.e., the suspected tumor.

The instrument 24 includes means to be described later which is arranged to sort the amplified electrical signals representative of the photons received by the probe by energy. As can be seen clearly in FIGS. 1 and 2 the instrument 24 basically comprises a lap-top microcomputer 30 which has been modified to include a multichannel analyzer and associated components (all to be described hereinafter). In particular, the instrument 24 includes the heretofore identified input connector 30A, the heretofore identified preamplifier/amplifier circuitry 30B, a conventional keyboard 30C, a floppy disk drive 30D, a hard disk drive and/or Read-Only-Memory ("ROM") drive (not shown), a trackball 30E or other pointing device, a color or monochrome display panel 30F, a loudspeaker or other annunciator 30G, an ON/OFF switch 30H, and various software or programs, files, etc., which the lap top computer uses for performing the various functions of the subject invention. It should be pointed out that such software, programs, etc., can be replaced by hardware or firmware to achieve the same ends.

The probe 22 described earlier is preferably constructed so that it has sufficient energy resolution to discern the characteristic x-ray signals and full-energy gamma-ray signals despite the continuum arising from Compton-scattered photons in some clinical settings. Moreover, the use of a collimator should aid in discerning the desired gamma rays and characteristic x rays detected from the Compton continuum in such clinical settings, by allowing only those Compton-scattered photons which come from within the field of view set by the collimator, and which are of a direction that results in them reaching the detector, to be detected. However, in some applications further reduction of the effects of the Compton continuum is desired. For such settings, one preferred embodiment of this invention utilizes means to remove or strip away the data representing the continuum arising from Compton-scattered photons in the vicinity of the characteristic x-ray peak(s) and in the vicinity of the full-energy gamma-ray peak(s). The means for accomplishing that action is provided by curve fitting software which is well understood by users practiced in the art of nuclear instrumentation for medical and non-medical applications.

The multichannel analyzer forming a portion of the instrument 24 is designated by the reference number 30I and is of conventional construction. For example, the implementation of the multichannel analyzer in the instrument 24 can be effected by use of a plug-in printed circuit card assembly for a personal computer ("PC Card") or PCMCIA card. One such PC Card is the multichannel scaler card sold under the trade designation MCS-PLUS by EG&G Ortec of Oak Ridge, Tenn. Alternatively, the analyzer may be constructed like that sold by Aptec Nuclear, Inc. of North Tonawanda, N.Y. 14120-2060, under the trade designation ODYSSEY 4. In any case the analyzer (30I) preferably has at least 256 channels for sorting the input signals from the probe 22 according to the energy of the photons detected. To that end, each channel of the analyzer has an energy width (e.g. about one keV) in order to provide suitable energy resolution of photons of various energies which are detected by the probe 22. The computer making up the instrument 24 is connected to the multichannel analyzer's output (not shown) to receive signals indicative of the energy of the photons picked up by the probe and is equipped with commercially available software, to be described later, resident on the hard disk or in ROM. This software, in combination with the hardware of the computer, establishes the following functional elements of the instrument 24: peak identification means 30J, window setting means 30K, characteristic x-ray isolation means 30L, full-energy gamma-ray isolation means 30M, ratio calculation means 30N, subtraction calculation means 30P, spectral line shape recognition means 30Q, characteristic x-ray and full-energy gamma-ray normalization means 30R, bar graph display and numeric display drive means 30S, and annunciator drive means 30T.

Before describing the details of the various means making up the instrument 24 a brief discussion of the mode of use of the system 20 is in order. To that end the surgeon places and orients the probe 22 to the desired position adjacent the suspected tumor site. The surgeon uses the probe to detect emitted photons initially by very slowly moving the probe 22 in contact with the exposed tissue plane over areas of interest, while listening to the audible signal produced by the annunciator 30E and/or while observing the bar graphs and photon counts provided on the visual display panel 30F. These bar graphs display the number of photons being detected. The surgeon then takes timed measurements of detected photons at sites of interest over fixed periods of time, e.g., five, ten, twenty, or thirty seconds, or some other period of time.

As earlier, the time period for said timed measurements, and the amount of radiotracer injected into the patient must be such that the numbers of emitted photons detected and displayed, and the differences and/or ratios of said numbers of photons which are used to determine the presence or absence of specific uptake represent statistically significant differences that will provide the practitioner with a sufficient confidence level.

During this "sampling" period, the multichannel analyzer 30I receives signals from the preamplifier amplifier circuitry 30B. The peak voltage of each signal received during the sampling period corresponds to the energy of each photon detected by the probe 22. Specifically, the multichannel analyzer 30I stores in memory each signal it receives from the probe 22 during the sampling period and assigns each of those individual signals to a particular channel within it based on the signal's associated voltage. As additional photons are detected by the probe 22 they are distributed into the various energy channels in the multichannel analyzer. The multichannel analyzer generates an electrical output signal, which if plotted, constitutes a spectrum or histogram of the number of counts of photons detected as a function of their energies.

Figure 14:
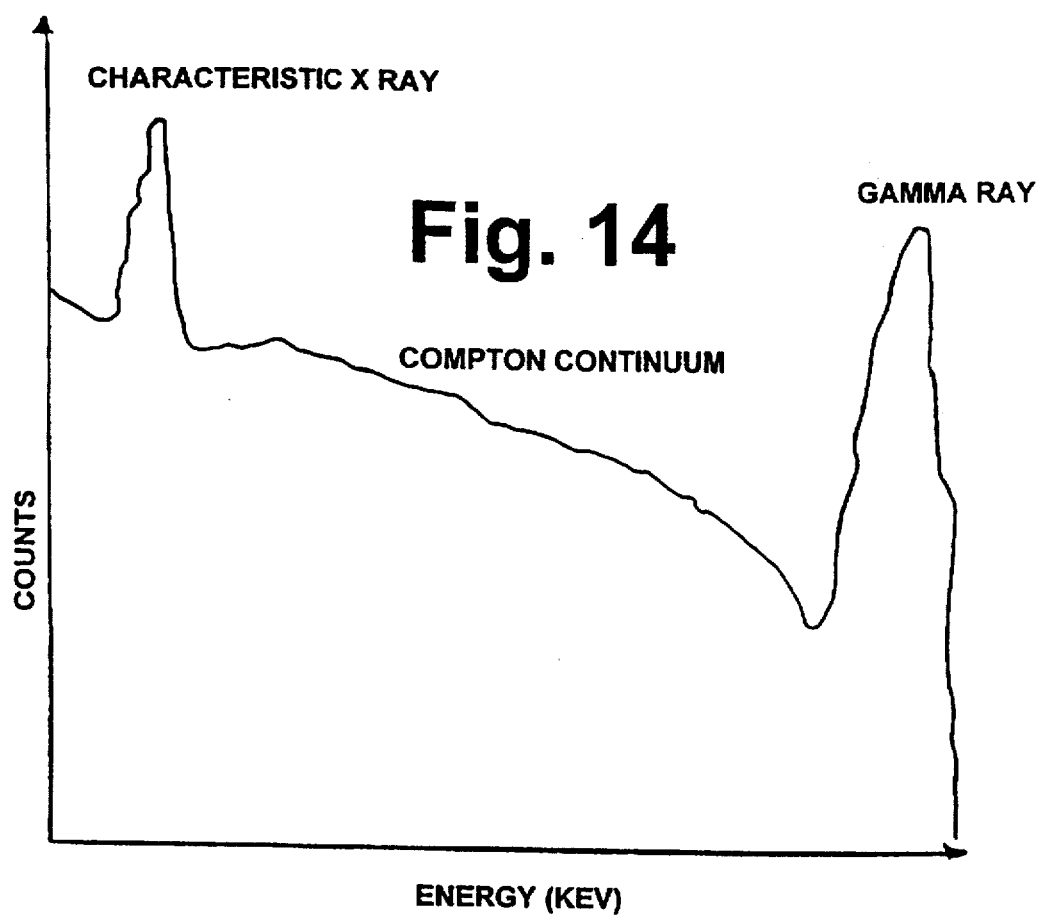
FIG. 14 is a histogram, like FIG. 12, but showing the spectrum of radiation counts obtained by the system of FIG. 1 during the localization of the tumor in accordance with one aspect of this invention.

A typical spectrum plot for Technetium 99 m is shown in FIG. 14. The spectrum plot represents graphically the accumulation of photons detected from Technetium 99 m radiolabelled tissue by the probe 22 over a fixed time period, and is comprised of three components, i.e., at least one full-energy gamma-ray peak, at least one characteristic x-ray peak, and the continuum arising from Compton-scattered photons. The y-axis of the spectrum plot represents the number of events, i.e., the number of photons detected within a given time period at a given energy, while the x-axis represents the energy of detected photons. It should be understood that the spectrum plot illustrated in FIG. 14 is comprised of raw data. That is, the spectrum plot represents all photons detected by the probe 22 within its field-of-view, i.e., all detected characteristic x-ray photons, full-energy gamma-ray photons, and Compton-scattered photons. These include photons originating from sites of specific uptake that are of clinical interest, and may as well include photons originating from background, such as circulating blood and bone marrow.

The output of the multichannel analyzer or histogram is provided to the peak identification means 30J. This means is arranged to determine if the number of photons detected are above a baseline generally corresponding to the Compton continuum, in order to identify the characteristic x-ray and full-energy gamma-ray peaks. The peak identification means can be implemented by any suitable software resident in the computer 30.

The output of the peak identification means 30J is provided to the window setting means 3OK. This means, which is also implemented by suitable software resident in the computer 30, establishes the upper and lower energy limits so as to establish the width of the energy band or window encompassing the characteristic x-ray peak and the energy band or window encompassing the full-energy gamma-ray peak.

The output of the window setting means is provided to the characteristic x-ray isolation means 30L and the full-energy gamma-ray isolation means 30M. These means, which will be described later, effectively strip or remove substantially all of the effects of Compton-scattering from the numbers of photons whose detection is displayed. While this function is of considerable importance in many applications, in others it is not. With regard to the latter, in order to determine the site(s) of specific uptake in accordance with this invention it is not necessary in some cases of clinical importance to first remove the continuum arising from Compton-scattered photons from the displayed data in the region of the characteristic x-ray and full-energy gamma-ray peaks. One example would be superficial tumors in depth-limited locations, such as ovarian cancer implants on the anterior or lateral inner peritoneal surface of the abdominal cavity. In such a case, the probe could be positioned against the suspected tumor from inside the abdominal cavity, and the detected far-field radiation would originate from the skin of the exterior abdominal wall, and consequently would include little Compton-scattered radiation. Melanomas of the hands and feet may also not require removal of the display of Compton continuum in order to identify characteristic x-rays.

However, in many instances it will be desirable to substantially strip the data representing the detection of the Compton-scattered photons away from the data at least in the region of the characteristic x-ray and full-energy gamma-ray photon emissions. Consequently, the preferred embodiment of this invention, shown herein, includes a Compton-stripping or neutralizing feature. This action is accomplished by the characteristic x-ray isolation means 30L and the full-energy gamma-ray isolation means 30M. Those means are comprised of computer software for performing mathematical curve fitting and stripping functions. In particular, the characteristic x-ray isolation means 30L and full-energy gamma-ray isolation means 30M when operating in the computer 30 serve to filter out the fraction of events that represent Compton-scattered photons, and pass through for display the data on characteristic x-ray photons and full-energy gamma-ray photons.

In accordance with a preferred embodiment of this invention the isolation of characteristic x-ray and full-energy gamma-ray photons by the means 30L and 30M can be accomplished by readily adapting existing commercial curve fitting and curve stripping mathematical software. Such modified software is resident in the computer 30 of the instrument 24, e.g., stored on the hard drive, on Read-Only-Memory, or on a card in the computer. Examples of usable or readily adaptable commercial software are the software sold under the trade designation PCA-II Second Generation Software by Oxford Instruments, Inc., Nuclear Measurements Group, of Oak Ridge, Tenn. 37831-2560, the software sold under the trade designation SIGMASTAT statistical software by Jandel Scientific Software of San Rafael, Calif. 94912-7005, and the software sold under the trade designation MATLAB and MATLAB Toolboxes by The Mathworks, Inc. of Natick, Mass. 01760-9889.

An alternative and simpler manner of substantially removing the data on detected Compton-scattered photons can be achieved by modifying the isolation means 30L and 30M to examine the data within a narrow energy range or "window" just above the highest energy displayed in the characteristic x-ray photopeak. In particular, the software of the instrument 24 can be arranged to examine the data on detected photons within a predetermined energy bandwidth, e.g., a 4 keV, "window" immediately above the energies of the characteristic x-ray peak. The data within that window can then be subtracted from the data on photons detected within a similar sized window encompassing the characteristic x-ray peak to provide a somewhat crude removal of Compton-scattered photons. A similar technique can be used to strip Compton-scattered photons from the vicinity of the trailing edge of the gamma-ray photopeak. If more precise stripping is required or desirable in the vicinity of the characteristic x-ray peak, the software can be arranged so that the data from a second predetermined width, e.g., 4 keV, window lying just below the energy displayed in the characteristic x-ray peak is examined. Then the mean of the numbers of photons detected in the window immediately above, and the window immediately below the energies of the x-ray peak is calculated and subtracted from the number of photons detected in the window making up the x-ray peak to result in a more precise stripping of the Compton-scatter.

Where higher resolution or precision is desirable, another approach is to use the isolation means 30L and 30M to mathematically fit a function using conventional curve fitting techniques to the portion of the histogram representing Compton-scattered photons and to subtract that function from the histogram of detected photons, thereby resulting in a substantially Compton-stripped signal or histogram representing primarily the characteristic x-ray photons and full-energy gamma-ray photons.

With the Compton continuum substantially stripped away, the analyzer provides the line shape of each peak, and also a measure of the number of characteristic x-ray photons and full-energy gamma-ray photons detected within the sampling period. The instrument 24 presents this information to the practitioner in visual and audible form. In particular, the information is displayed visually in the form of two bar graphs depicting the numbers of the characteristic x rays and full-energy gamma rays detected within a given time period, and associated numeric displays of the same on the video screen 30F. This is shown clearly in FIGS. 1 and 9–11. As can be seen therein, a light bar or graph 32A whose length represents the number of characteristic x rays detected, and a light bar or graph 32B whose length represents the number of full-energy gamma-ray counts received are displayed on the video screen or panel 30F. In accordance with a preferred embodiment of this invention the bar graphs 32A and 32B are normalized to the naturally occurring abundance of characteristic x rays to full-energy gamma rays for the particular radioisotope used, so that when photons are detected in the correct ratio for the natural abundance of characteristic x rays and full-energy gamma rays for the particular radioisotope, the two bar graphs will be of the same length (as shown in FIG. 1). Associated with the bar graph 32A on the video screen 30F is a numeric display 34A representing the characteristic x-rays detected, while a similar numeric display 34B representing the number of full-energy gamma rays detected is associated with the bar graph 32B. The bar graphs 32A and 32B and the associated digital displays 34A and 34B, respectively, are produced under control of the bar graph and digital display driver 30S. This driver is implemented by any suitable software in the computer 30.

The information regarding the photons detected is provided audibly by the annunciator 30G, e.g., a speaker or tone or voice synthesizer, under the control of the annunciator driver 30T. The operation of these means will be described later.

The practitioner can utilize the information on the display screen 30F and the information provided by the annunciator 30G in ways to be discussed below, to determine the locations and to evaluate the depth of sites of specific uptake.

In some preferred embodiments of this invention, as will be discussed later, a library of spectra of Technetium 99 m, Indium 111, Iodine 123, Iodine 125, Iodine 131, Thallium 201, Gallium 67, Fluorine 18, and other such radionuclides of interest is assembled and resident, e.g., stored within the computer of the instrument 24. Available data, such as that provided by performing point source measurements of radiation passing through a water equivalent tissue material or water itself, from two millimeter increments of depth or "thickness" to water depths of 30 millimeters, and at five millimeter increments for depths from 30 to 200 millimeters is preferably obtained from empirical measurements or available data. In any case a library of data on the various radioisotopes is stored in the instrument 24 or on diskette for input into the instrument. This makes available to the system 20 a reference library of information on the effect of the thickness or depth of tissue through which emitted radiation passes on such factors as: attenuation of characteristic x rays and full-energy gamma rays; the line shape of the spectra of full-energy gamma-ray peaks and characteristic x-ray peaks; and the ratio of full-energy gamma rays to associated characteristic x rays. All of that data will be useful for localizing a site of specific uptake, e.g., a tumor, as will be described later.

The window setting means 30K assists in locating sites of specific uptake and obtaining other information regarding structures within the body by electronically selecting for evaluation a specific energy range of the immense amount of photon information within the probe's field of view. However, before describing the window setting means 30K the following discussion of the problems in discriminating sites of specific uptake is in order. To that end, and as will be appreciated by those skilled in the art, as the distance measured along the central longitudinal axis of the probe 22 from its window increases, the number of potential sites from which emitted photons can be detected increases. That is, with increasing distance a probe's field-of-view will typically contain an increasing amount of received emissions. By evaluating the entire field-of-view, it may be extremely difficult to determine the exact location of the site of specific uptake. For example, gamma-ray photons are capable of traveling relatively great distances, i.e., tens of centimeters, through soft tissue without being absorbed. Since it is possible for full-energy gamma-ray photons to originate from distant sites of specific uptake, as well as from distant sites of non-specific uptake, located deep within field-of-view, it is difficult to determine with a high degree of certainty the exact site from which such gamma-ray photons originate.

Conversely, characteristic x rays are typically comparatively low energy emissions that can travel only ten (10) to thirty (30) millimeters through soft tissue before being absorbed. For example, the half-value layer in water (i.e., the thickness which will absorb one-half of the incident x rays) for 20-keV x rays is about ten millimeters; for 30-keV x rays, 21 millimeters; and for 40-keV x rays, 28 millimeters. For point sources, the inverse square law also operates, further limiting depth of detectability. In addition to absorption, photons passing through tissue (or water) can also be Compton-scattered, but not absorbed. The photons arising from this scattering process have lower energies by virtue of having been scattered. Both absorption and Compton-scattering result in a reduction of the number of photons recorded in a given x-ray peak.

The energies of the characteristic x rays of Indium 111 are about 24 keV, and of Technetium 99 m are about 19 keV; therefore very few are detectable beyond a tissue depth of 30 millimeters. Detected characteristic x-ray photons from these radioisotopes will therefore originate from tissue lying at shallow depths within the field of view, such that the location of the site of their origin will be within a much smaller and better-defined volume of tissue than would be the case for tissue located by the detection of higher energy gamma-rays alone.

The subject invention enables the surgeon to examine the characteristic x-ray photons received by the probe to determine that the site of specific uptake, e.g., a radiolabelled site of suspected tumor, is located at a shallow depth beneath overlying tissue by making use of the fact that the characteristic x-rays of the radiotracer only travel a short distance through tissue. For example, the characteristic x-rays of Technetium 99 m have a half value layer of 8 millimeters, i.e., the number of 19-keV x rays of Technetium will drop by half through 8 millimeters of water.

The "very near-field" of the disclosed embodiment of this invention can be defined as two half value layers of water-equivalent tissue, wherein the received number of characteristic x-ray photons will be 100% to 25% of the number emitted. The "intermediate-field" can be defined as being tissue lying at depths greater than two, but less than four, half value layers beneath the exposed or exterior tissue plane, wherein the received number of photons will be from 25% to 6% of the number emitted. As discussed before, the very near field and the intermediate field together constitute the near field. The "far-field" can be defined as being located at or beyond four or more half value layers from the site of nuclear uptake for the characteristic x ray(s) of interest. In the far field the detected number of characteristic x rays will be very small, less than 6% of the number of characteristic x rays emitted from uptake sites at tissue depths greater than four half-value layers. Thus, for Technetium 99 m the very near-field (or two half value layer) distance is approximately 0–17 mm, the intermediate-field is 17–33 mm, the near field (including both the very near and the intermediate fields) is approximately 0–33 mm., and the far-field is beyond 33 mm.

It should be pointed out that other ranges for the very near-field, intermediate-field, and far-field can be used with the subject invention, and the range of each of the fields as given above is merely exemplary. Moreover, the very near-field, intermediate-field, and far-field ranges, being a function of the energy level of the radiotracer, differ from radiotracer to radiotracer. For example, Indium 111 emanates characteristic x-ray photons at an energy of 24 keV, and at an abundance of 83.5%. Thus, if the same definitions are used as were given in the foregoing example, the very near-field for Indium 111 would be 0–27 mm, the intermediate-field would be 27–54 mm, and the far-field would be beyond 54 mm.

As mentioned above, the window setting means 30K of the instrument 24 serves to electronically select for evaluation a specific energy range or portion of the photons detected that falls within the probe's field-of-view 12. That is, by adjusting the window setting means, the practitioner can elect to examine only photons falling within a predetermined range of energies, i.e., select only characteristic x-ray photons which originate from tissue lying at shallow depths within the tissue (near-field radiation), or select a combination of the characteristic x-ray photons and the full energy gamma-ray photons which originate from tissue within the near-field. By using both the window-setting means and the ratio-calculation means the practitioner can select only the full energy gamma-ray photons which originate from tissue beyond the intermediate-field, i.e., with the far-field.

The window setting means is implemented by adapting the previously mentioned software in ways known in the art to enable the practitioner to select one or more of many preselected ranges of energy levels in order to evaluate only characteristic x rays of one (or more) energies and/or full-energy gamma rays of one (or more) energies from those detected by the probe 22, and thereby select and display data for photons emitted from one (or more) particular preselected range of tissue depths. For example, in accordance with one mode of operation of the present invention, in the case where a practitioner believes that an area of specific uptake may be located close to the surface of the overlying tissue, by adjusting the instrument's window setting means 30K, the practitioner can suppress information on extended field gamma-ray photons which cause ambiguity, and thus evaluate only characteristic x-ray photons that originate from points located only in close proximity to the exterior or external tissue surface (from the near field), e.g., often no more than ten (10) to thirty (30) millimeters deep. By using the signals from these characteristic x-ray emissions in ways to be discussed later, the practitioner is able to determine with a considerable degree of certainty the locations of cancerous tissue lying at shallow depths. In this way, by using radiotracers which emit gamma rays that have energies greater than 60 keV ("imaging radiotracers"), which can be used to form images in gamma cameras, and which also emit characteristic x rays of lower energies, the practitioner can have the following benefits. The practitioner can have preoperative gamma camera images, to assist in the surgical search for sites of specific uptake, and also use a radiation detecting means during surgery to locate sites of uptake at shallow tissue depths, without having the intraoperative search for said shallow sites compromised by signal from far-field radiation, such as background radiation from deeper sites of uptake.

In order to accurately localize near-field suspected tumors the instrument 24 may make use of the ratio calculation means 30N. For any radioisotope, the ratio of gamma rays to x rays is known and constant; in instances of a plurality of either gamma rays or x rays from a specific radioisotope, each such ratio between gamma rays or x rays of one energy and the gamma rays or x rays of another energy are likewise known and constant. The ratio detected from a specific radioisotope as the radiation passes through different thicknesses of tissue changes, in accordance with the absorption of photons of differing energies as they pass through a substance, as described on page 21. These known ratios are stored in the instrument in the aforementioned reference library. For example, Technetium 99 m provides a natural abundance of 7.5% 19-keV characteristic x-rays and 89% 140-keV full energy gamma-rays. Indium 111 provides a natural abundance of 83.5% 24-keV characteristic x rays, 89.6% 172-keV full-energy gamma rays, and 93.9% 247-key full-energy gamma rays. The ratio calculation means 30N serves to calculate the ratio of characteristic x rays detected versus gamma rays detected within a given period of time for a particular radioisotope, and to compare that calculated ratio with the stored reference ratios for specific, different depths of tissue, and for no depth of tissue. For cases in which either no background radiation, or a low level of background radiation is detected within the field of view associated with a site of specific uptake located at a shallow depth, information based on this ratio can be used by the practitioner to more closely establish the depth of that site. The implementation of the ratio calculation means 30N is easily accomplished by modification of the aforementioned commercially available computer programs.

The subtraction calculation means 30P works in cooperation with the ratio calculation means 30N to provide additional depth (z-axis) information about tissue with nuclear uptake. In particular, the means 30P subtracts the number of detected full-energy gamma-rays which correspond to the number of detected x rays from the total number of detected full-energy gamma rays, to result in a measure of far-field radiation emitted by tissue lying at depths beyond that from which the detected characteristic x-rays were emitted. The far-field radiation may be from both non-specific background radiation, and from specific uptake of deeper-lying tissue. The practitioner can use this information on far-field radiation, for example, to evaluate uptake in deeper tissues, and to identify sites of high background radiation, in order to be able to orient the probe in such a way as to avoid or minimize the effects of such background radiation on near-field measurements, such as measurements made using the aforementioned ratio calculation means to more closely establish the depth of a site of specific uptake at shallow depths.

If the practitioner simultaneously uses more than one radioisotope in the radiotracer, or more than one radiotracer, each with a different radioisotope, where the relative uptake of the two radiotracers are known and predictable, then the ratio calculation means 30N and the subtraction calculation means 30P can be further used to obtain additional information on the depth of tissue with nuclear uptake. For example, if the radioisotopes to be used are Technetium 99 m, which emits characteristic x-rays at approximately 19 keV, and Iodine 123, which emits characteristic x-rays at approximately 27 keV, then the 27 keV x-rays would be detected from tissue lying at greater depths than the tissue from which the 19 keV x-rays were detected. By using the same methodology discussed above in connection with the subtraction means, the radiation detected can be divided into Technetium 99 m near-field (emitted by tissue from which 19-keV x rays are detected), Technetium 99 m-Iodine 123 intermediate field (emitted by tissue from which 29-keV x rays are detected but not 19-keV x rays), and Iodine 123 far field (emitted by tissue from which gamma rays are detected but not 29-keV x rays). The practitioner can then use this information, for example, to further establish the depth and thereby better establish the lateral X, Y location and depth Z coordinates of the various tissues in which the uptake is found.

The same method may be used to further segment the depth of the radiation field, by using radioisotopes exhibiting more than one gamma and/or characteristic x-ray peak, wherein the photon energies generally involved lie below about 100 keV; an example of one such radioisotope is Thallium 201, which emits x-rays at about 70 and 81 keV. By applying the ratio calculation means together with the subtraction calculation means to a multiplicity of x-rays and/or gamma-rays, the invention allows the practitioner to further segment the depth of the layers of tissue in which uptake is detected, and thereby more closely locate the tissue uptake site(s) of interest.

In accordance with a preferred embodiment of this invention, the instrument 24 also includes the heretofore identified spectral line shape recognition means 30Q. As is known, the numbers of photons detected, or the numbers of counts, in the characteristic x-ray and gamma-ray peaks for a particular radioisotope are dependent upon several factors, including the density and atomic number of material through which photons must travel prior to detection, e.g., blood, soft tissue, lung tissue, or bone, and the distance the photons must travel through that material prior to being detected by the probe 22. Soft tissue, blood, and most tumors have similar densities, i.e., approximately that of water. Bone is much denser. Lungs, because of their large air content, have effective densities much less than water. Therefore, when gamma-ray photons and x-ray photons travel through relatively dense materials, e.g., bone, prior to detection, the attenuation will be disproportionately high for the lower energy x rays. In this regard the linear attenuation of bone at 20 keV is approximately nine times that of muscle, while muscle is very close to water in linear attenuation. Consequently, the number of x-ray photons detected will be relatively low or non-existent when passing through bone. Conversely, when x-ray and gamma-ray photons travel through less dense materials, e.g., soft tissue, the number of characteristic x rays detected and displayed in the spectrum will be relatively high. The typically higher energy gamma rays will suffer similar attenuation effects, but to a lesser degree.

By storing in the instrument 24 a library of reference data representing the line shapes of the spectra for various radioisotopes, as a function of the thickness and types of intervening tissues, as discussed on page 34, the instrument 24 is able to provide the practitioner with information to localize the suspected tumor.

Figure 12:
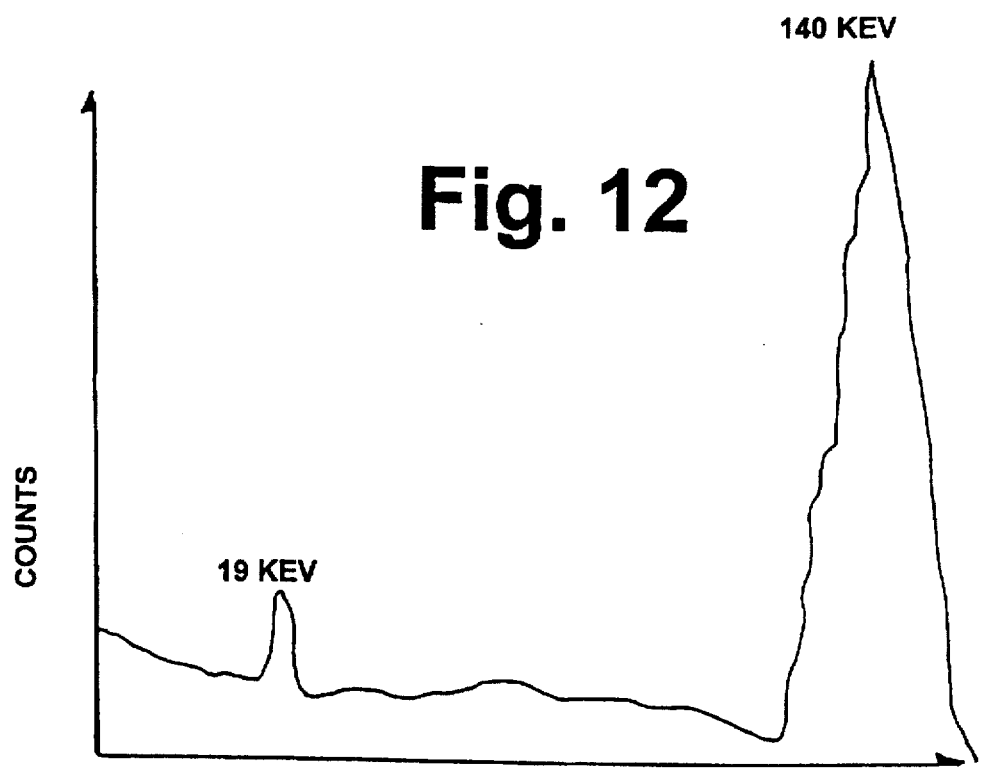
FIG. 12 is an exemplary graphical representation or histogram of the spectrum of the radiation counts obtained by the system of FIGS. 1 and 2 from a Technetium 99 m radiotracer through air.
Figure 13:
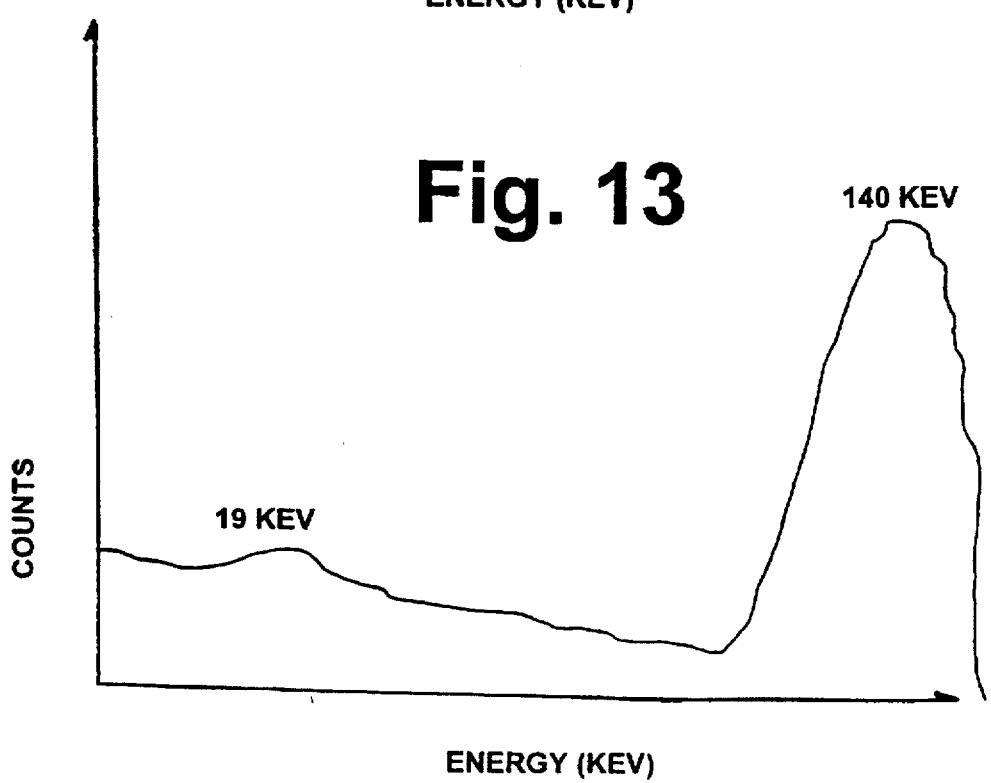
FIG. 13 is a histogram, like that of FIG. 12, but of the radiation counts received through a reference distance of water equivalent tissue.

In FIG. 12 there is shown the spectra of photons from a Technetium 99 m tagged source passing through air to a probe a predetermined distance away. FIG. 13 represents that spectrum with a known material, e.g., water (to represent water equivalent tissue), of a known thickness therebetween. As can be seen, the trailing or lower energy edge of the full energy gamma-ray photopeak has become asymmetrical and wider, and the maximum of the peak has been reduced. The data representing both of the spectra of FIGS. 12 and 13 as well as other data for other thicknesses of intervening body materials, e.g., muscle, tissue, bone, lung, etc., are stored in the reference library in the instrument 24. These data are used by the line shape recognizing means 30Q to compare to the spectrum of the photons actually detected by the probe 22 and processed by the multichannel analyzer and associated means described above. In particular, the line shape recognizing means looks for the closest fit, and once that is achieved the instrument 24 provides the practitioner with information visually on the display screen 30F and/or audibly by the annunciator 30G on the depth of the tissue exhibiting the detected specific nuclear uptake. Thus, by examining the degree of asymmetry of the gamma-ray peak actually measured to that of the reference library, the depth of tissue of known density above the site from which the photons were emitted is determined.

The practitioner may make use of the increase in gamma-ray or x-ray peak line shape asymmetry as tissue depth or density through which the gamma-rays or x-rays pass increases. In this regard, if the distance to the site of specific uptake is known or can be estimated to a reasonable degree of assurance by some independent means, then by using the data in the stored reference library, the instrument may provide the practitioner with information for estimating density of tissue intervening between the site of specific uptake and the probe. One example of the use of density information would be for a site of uptake known to be at a shallow depth, such as a tumor penetrating from within the bone marrow cavity, through to the surface of the bone. In this example, the practitioner could thus know in advance where less force would need to be applied to pierce thin or broken overlying cortical bone while using a needle to obtain a diagnostic biopsy. Such determinations could be of great benefit in reducing inadvertent penetration of the far side of the bone during such procedures.

The spectral line shape measurements which are made to establish the reference data for use by the spectral line shape recognizing means 30R can be made with solid state semiconductor detectors, such as Cadmium Zinc Telluride, Silicon, or Germanium, at room temperature or cooled below room temperature.

As discussed earlier the instrument 24 is equipped with the annunciator 30G. The annunciator is driven by the annunciator driver 30T to provide audible signals to aid the practitioner as he or she uses the probe to localize the suspected tumor. In particular, the driver 30T drives the annunciator to cause it to provide audible sounds which are modified in various ways, e.g., in pitch, in intensity, in repetition rate, or in some other way or combination of ways, as a function of the rate at which the characteristic x-ray photons and/or full-energy gamma-ray photons are being detected. The sound production provided by the annunciator 30G is known in the prior art and has been available on several different commercially available surgical gamma probe systems. The driver 30T for the annunciator may be implemented by any suitable software. For example, when the invention is being used to detect characteristic x rays exclusively, the annunciator's driver 30T may be set to emit a specific form of signal, e.g., "beeps", only upon detection of characteristic x-ray photons by probe 22. Specifically, when the probe 22 is directed toward a volume wholly comprised of clean tissue, i.e., away from a location of specific uptake, the probe 22 will detect a relatively low rate of characteristic x-ray photon emissions (because only a relatively dilute concentration of radiotracer will exist within the probe's field-of-view). Therefore, the annunciator 30G will emit beeps at a slow rate indicating that probe is detecting clean tissue only.

Conversely, when probe 22 is directed toward a shallow site of specific uptake i.e., a location containing cancerous tissue, the probe 22 will detect characteristic x-ray photons emitted at a greater rate as the result of a higher concentration of radiotracer existing at the site of specific uptake. Thus, the beeps emitted from the annunciator under the control of driver 30T will change dramatically in frequency, thereby indicating that a site of suspected specific uptake has come within the field-of-view of probe.

In an alternative embodiment, the annunciator 30G under the control of its driver 30T can produce tones and/or chirps to be utilized alone or in conjunction with beeps to audibly distinguish areas of suspected specific uptake from areas of clean tissue. The annunciator driver may be arranged so that it can be adjusted by the practitioner to cause the annunciator to emit beeps upon the detection of lower energy (typically characteristic x-ray) photons and simultaneously to emit chirps or other audibly distinguishable tones upon the detection of higher energy (typically gamma-ray) photons. If desired a voice synthesizer can be used to provide verbal information to the practitioner.

The method of use of the system 20 to localize a suspected tumor site tagged with Technetium 99 m will now be described with reference to FIGS. 3–11.

To determine the location of Technetium 99 m tagged lesions lying at shallow depths below the exposed or external tissue plane, i.e. within the "near-field", one can examine the characteristic x-ray photons while ignoring the gamma-ray photons being received. By examining these photons, the system enables the user, e.g., a surgeon, to center the probe over a near-field site of uptake, e.g., a suspected tumor or lesion.

To determine the location of suspected tumors in the near field, especially in the deeper (or intermediate) portion of the near field, the surgeon can also use the system of this invention to examine both the characteristic x-ray photons received and the full-energy gamma-ray photons received, and compare numbers of each detected, thereby obtaining information regarding the depth of the suspected tumor within the near field.

In addition, to determine the location of suspected tumors deeper within the tissue, i.e. within the "far-field", the system of this invention can examine the number of full energy gamma-rays detected, and subtract the number of detected gamma rays which correspond to the number of characteristic x-rays detected for the radioisotope in use, resulting in a count of gamma rays originating from the far-field only, from tissue depths from which no emitted characteristic x rays can be detected.

Of significant importance to this invention is the fact that the skilled practitioner is able to determine whether the gamma-ray photons received are from a distant uptake source, e.g., a kidney within the probe's field of view, or from a nearby radiolabelled source, e.g., a possibly cancerous lymph node, within the probe's field of view. In this regard, if the proportion between the characteristic x-ray photons received to the gamma-ray photons received is appropriate for a nearby source then one can rely on the statistics of the nearby gamma-ray photons received. In this regard, as mentioned above, the 19-keV characteristic x rays of Technetium 99 m have an abundance of 7.5%, and the 140-keV full-energy gamma-ray photons have an abundance of 89% Thus, the ratio of the natural abundance of characteristic x-ray photons to full energy gamma-ray photons is 7.5/89 or 0.084. Accordingly, if the ratio calculating means of the system detects a sufficient number of characteristic x-ray photons such that their ratio to the gamma-ray photons detected is 0.084, then the practitioner knows that both the gamma rays and the x rays being received are from a radiolabelled source lying at a shallow depth beneath the exposed tissue plane, and not from a deep source of uptake.

As noted earlier, the display panel 30F shows the number of characteristic x-ray photons and full-energy gamma-rays received by the lengths of the lighted portion of the light bars 32A and 32B, respectively, and by the associated numeric displays 34A and 34B, respectively. The light bars in this case are normalized for the appropriate ratio of characteristic x-ray photons to full gamma-ray photons for the radiotracer utilized, e.g, a ratio of 0.084 for Technetium 99 m, so that when an appropriate ratio of characteristic x-ray photons and full energy gamma-ray photons are received the lighted portions of the light bars will be of the same length, while the associated numeric displays show numerically the absolute number of photons detected during the measurement or "count" period. The annunciator, in response to the driver 30T, produces respective sounds representing the rates at which the characteristic x-ray photons and full energy gamma-ray photons are detected. These sounds can be normalized by the annunciator driver, if desired.

The surgeon can use the displays and/or sounds produced to determine the location of the radiolabelled tissue. For example, assume that the surgeon is trying to localize a suspected tumor or lesion within the abdomen of a patient who had received a radiolabelled tracer, e.g., a monoclonal antibody tagged with Technetium 99 m. To accomplish that procedure the surgeon inserts the hand held probe 22 at some starting point, e.g., against some tissue plane, within the abdomen. The surgeon may then move the probe in the x, y, and z directions with respect to the suspected tumor site to find the probe location and orientation which yields the maximum number of characteristic x-rays detected, and compares the ratio of the two numbers to that expected for the radiotracer used. This procedure is graphically represented by the illustrations of FIGS. 3–9.

Turning now to FIG. 3, it can be seen that there is illustrated the situation wherein the nose or tip 22A of the probe 22 is located at a tissue plane in immediate proximity to the front surface of a radiolabelled site of suspected tumor, with the tumor being located within the probe's "field of view" (designated by the phantom lines).

The graphical representation of the number of characteristic x-ray photons received by the probe during the count period is displayed on the system's normalized light bar 32A, while the absolute number of photons detected is displayed on the associated numeric display 34A. In a similar manner a graphical representation of the number of full energy gamma-rays detected by the probe during the count period is displayed on the system's other normalized light bar 32B, while the absolute number of photons detected is displayed on the associated numeric display 34B. The annunciator, if enabled by its driver, will produce corresponding audible signals so that the practitioner need not look at the display panel 30F. If desired, the annunciator can be disabled so that no sounds are produced.

The following examples serve to illustrate the general methods involved in using radiation detecting means, as described by this invention, to locate sites of concentrated nuclear uptake. The actual numbers of photons detected must be sufficient to provide statistically significant data and thereby provide the practitioner with the appropriate level of confidence in said data, as described on page 26.

In the example of FIG. 3 the number of characteristic x-rays detected during the count period is 600 and the number of full energy gamma-rays detected is 7143. Thus, the ratio of the characteristic x-rays to the full energy gamma-rays is 600/7143 or 0.084. This ratio, being the ratio normally existing for characteristic x-rays and gamma-rays of Technetium 99 m, and which is stored in the reference library of the instrument 24, indicates that the data received are appropriate to a radiolabelled source with little or no intervening tissue (i.e., the ratio calculation means compares the detected photons to the reference photons to determine if the proper ratio exists). The light bars 32A and 32B in this case will each be of the same length, thus graphically displaying that the appropriate ratio exists. Thus, the surgeon is justified in believing, from the displayed information (as well as audible sounds, if enabled), that a site of significant uptake, e.g., the radiolabelled site of suspected tumor, is probably within the field of view of the probe and in close proximity to the exterior tissue plane against which the probe's nose 22A rests.

By moving the probe 22 laterally up or down (i.e., in the "y" direction) and right or left (in the "x" direction) and taking readings of the characteristic x rays detected in a given time period, or count rate, until a maximum count rate is attained, the surgeon is able to center the probe on the suspected tumor site. In this regard, when the count rate for characteristic x rays is maximized, at any distance from a shallow site of uptake, or along a given tissue plane, the axis of the probe will be aligned with the center of the that site, as determined by the measured amounts of nuclear uptake. Thus, by maximizing the count rate for characteristic x rays at any tissue plane at which the nose of the probe is located, one is able to establish the "x" and "y" coordinates of the center of a proximate suspected tumor for any given distance from that tissue plane.

Moreover, the count rate for characteristic x-rays in comparison to the count rate for full-energy gamma rays provides some indication of the distance, i.e., the "z" coordinate, from the front surface of the suspected tumor to the exterior tissue plane where the nose of the probe is located.

With many radiotracers, such as those involving monoclonal antibodies, there often are known, predictable locations of significant non-specific uptake. The following examples are based on conditions wherein the surgeon would know that the kidneys would be such sites of significant non-specific uptake.

As should be appreciated by those skilled in the art, if, in attempting to localize a radiolabelled site of suspected tumor, the system of the subject invention detects a number of characteristic x-ray photons which is disproportionately low relative to the number of gamma-rays for the radioisotope being used, then the surgeon would be justified in believing that the vast majority of the gamma-rays detected are emanating from distant, or far off, intense sources of uptake, deep within the tissue, rather than close-in areas of uptake, i.e., the suspected tumor. An example of this condition is shown in FIG. 4, wherein the probe 22 is shown centered over a Technetium 99 m tagged suspected tumor in a lymph node located very close to the nose of the probe, and with a substantial portion of the patient's kidney being in the probe's field of view, but significantly remote or deep within the tissue, e.g., five cm from the nose of the probe. Since the kidney typically absorbs a significant amount of the radiolabelled tracer, and in this example is five cm beneath the exposed tissue plane, the characteristic x-rays from the kidney have to pass through six half value layers of intervening water-equivalent tissue, whereupon only 1% of those x-ray photons reach the probe. The vast majority of the characteristic x-ray photons received by the probe, e.g., 600 in this example, will be from a nearby uptake source, in this case the suspected tumor. Since full energy gamma-ray photons are able to travel through much greater distances of intervening tissue without significant attenuation or absorption than are the x-rays, the number of the gamma-ray photons received will be quite high relative to the number of characteristic x rays received. In this example 20450 gamma-rays are detected. The resulting ratio of numbers of characteristic x-rays detected to numbers of gamma-rays detected is thus 0.029. This disproportionately low ratio is graphically represented by the normalized light bars being of different lengths, i.e., as can be seen in FIG. 4 the light bar 32B representing the gamma-rays is substantially longer than the light bar 32A representing the characteristic x rays, to indicate to the surgeon that the vast majority of the gamma-ray photons being received are probably from a remote, intense site of uptake (in this case a substantial portion of the kidney, the general location of which will be known to the surgeon).

Figure 5:
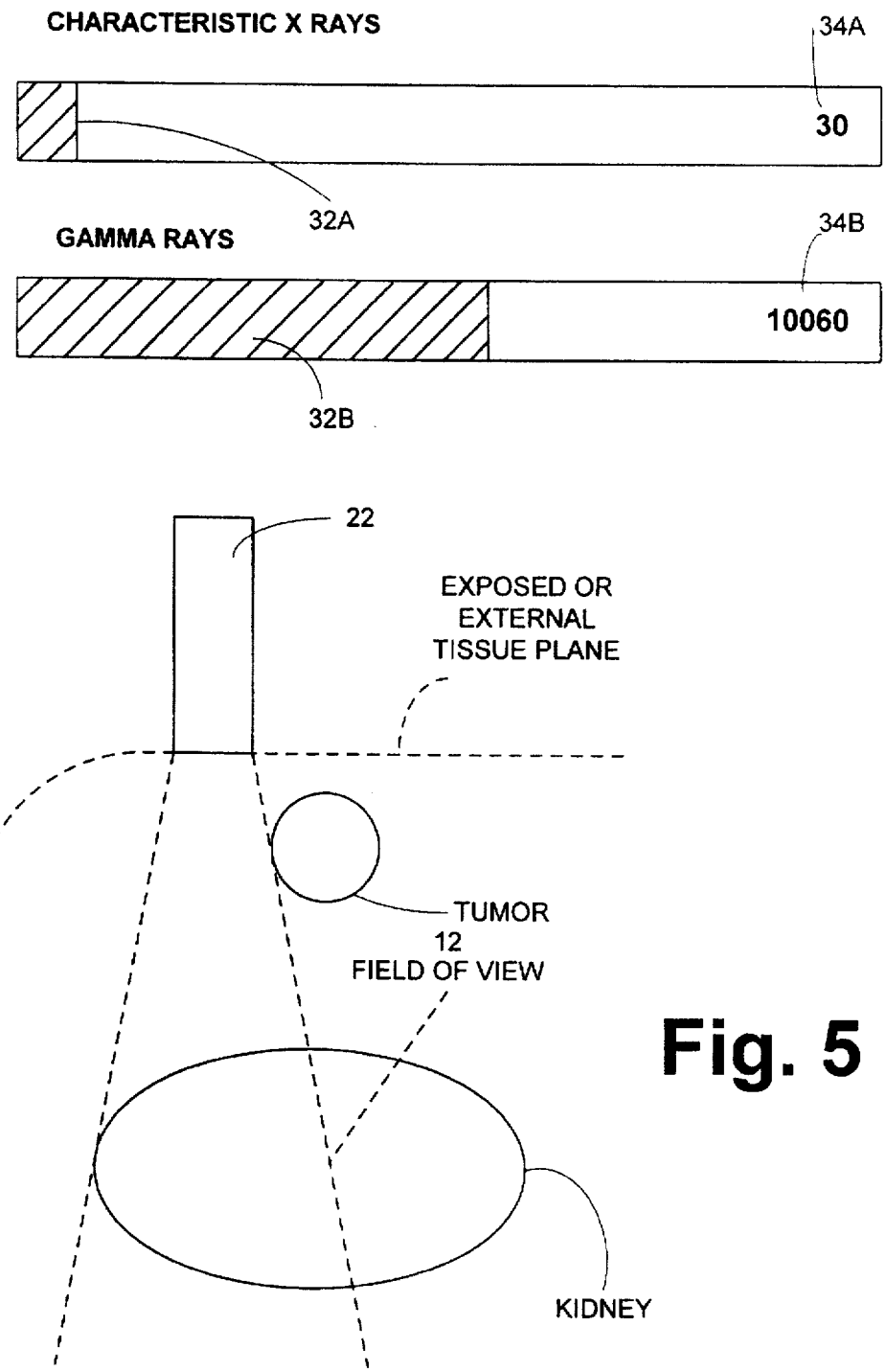
FIG. 5 is an illustration, like that of FIG. 4, but showing the system being used in a later step in determining the location of the radiolabelled tumor of FIG. 4.
Figure 7:
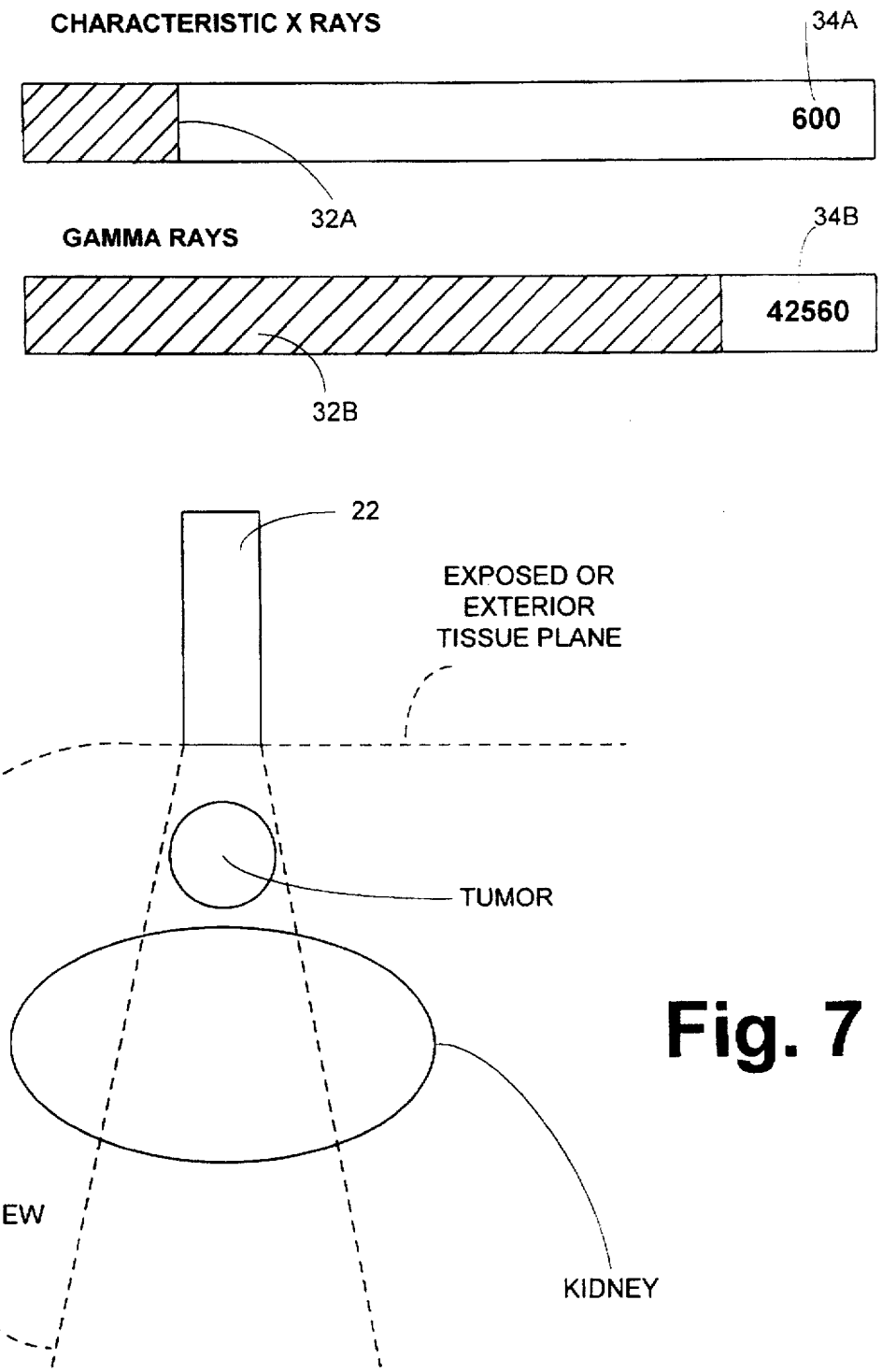
FIG. 7 is an illustration, like that of FIG. 3, but showing a portion of the system shown in FIGS. 1 and 2 being used to determine the location of a radiolabelled tumor located immediately adjacent a kidney in accordance with one aspect of the method of this invention.

Hence the surgeon must continue his/her search to maximize the numbers of characteristic x-rays detected in the desired ratio to the number of gamma rays detected in order to localize the suspected tumor. To achieve that end the surgeon can move the probe laterally along the exposed tissue plane, to the right and/or left (i.e.,in an "x" direction) and up and/or down (i.e., in the "y" direction) from its previous "on axis" position to take "off axis" control readings, and thus determine how the detected numbers of photons change. This enables the surgeon to locate the marginal edges of the suspected tumor, and to compare numbers of photons detected from the suspected tumor to those from the adjacent background. For example, as shown in FIG. 5, if the probe is moved to the left until the numbers of detected characteristic x-rays drop dramatically, e.g., drop from 600 to 30, while the numbers of detected gamma-rays drop from 20450 to 10060, this indicates that the suspected tumor is no longer within the probe's field of view, while a lesser (but still a considerable portion) of the remote area of uptake (e.g., a lesser portion of the kidney) remains within the field of view.

The surgeon then has to continue the search to localize the suspected tumor. To that end, if the surgeon moves the probe in the "x" direction to the left of the tumor, down in the "y" direction so that the suspected tumor is out of the probe's field of view (whereupon the numbers of characteristic x-rays detected in a given time period will drop dramatically) and then orients the probe at an angle to its original orientation until the numbers of detected characteristic x-rays increase dramatically and the numbers of detected gamma-rays drop dramatically, the surgeon is able to "home in" on the suspected tumor by eliminating the effects of the remote site of uptake, i.e., the kidney. This action is illustrated in FIG. 6, wherein the probe is shown oriented perpendicular to its original orientation so that 600 characteristic x-rays are detected, while 7143 gamma-rays are detected. In this case, the light bars 32A and 32B will be of the same length since the ratio of x-rays to gamma-rays is 0.084, thereby indicating the presence of a close uptake source, i.e., the lymph node with suspected tumor, with no other source of uptake (i.e., no portion of the kidney) in the field of view. The surgeon is thus able to localize the suspected tumor.

Figure 8:
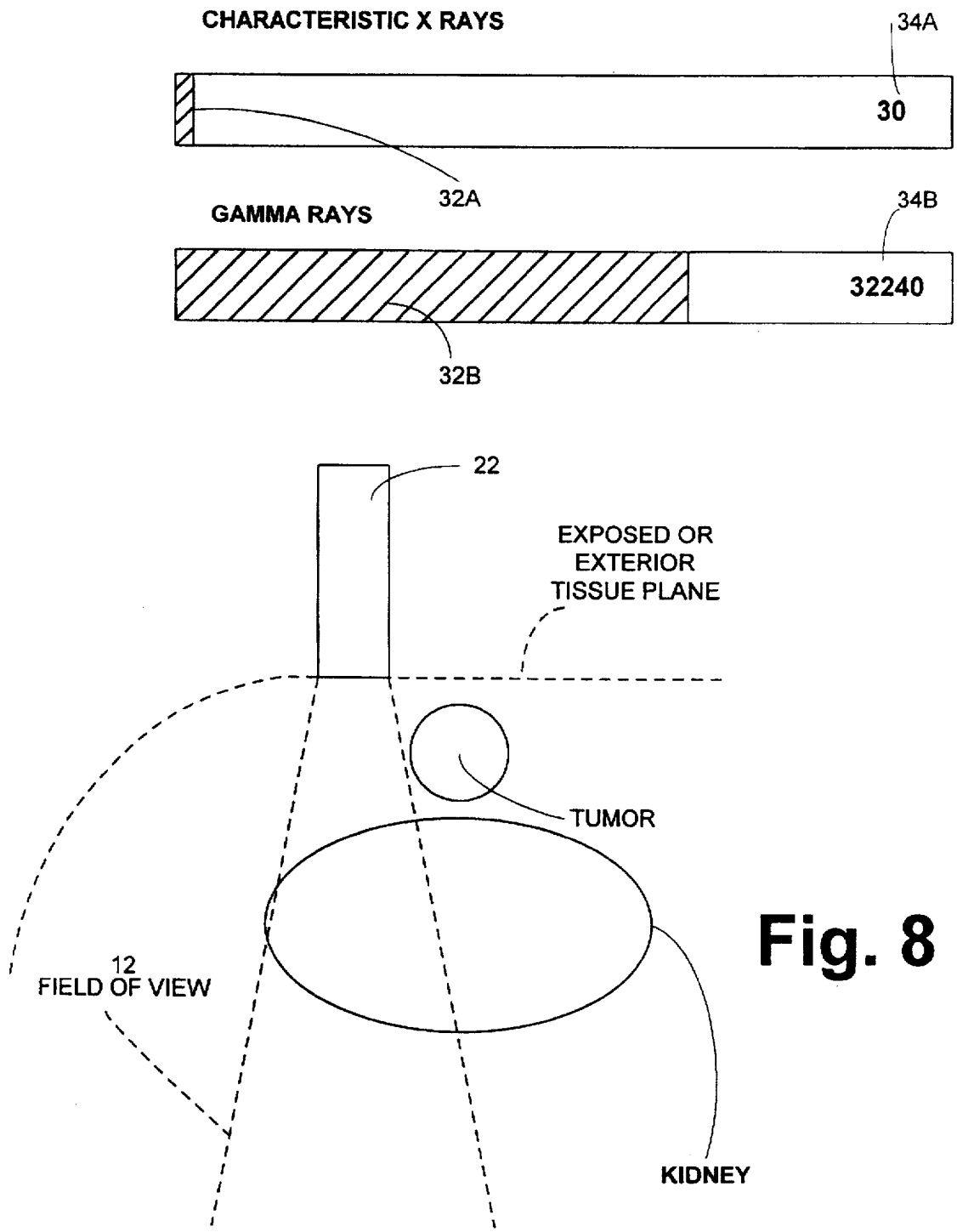
FIG. 8 is an illustration, like that of FIG. 7, but showing the system being used in a later step in determining the location of the radiolabelled tumor of FIG. 7.

As mentioned earlier, the probe 22 preferably includes a collimator 22E. That collimator may be adjustable or fixed, in order to decrease (or increase) the field of view of the probe's radiation detector or crystal 22C to facilitate the localization of the suspected tumor, e.g., to restrict the probe's field of view, thus making it easier for the surgeon to avoid detecting known sources of non-specific uptake. This feature may be of significant assistance in localizing suspected tumors, particularly those closely adjacent to intense sources of known non-specific uptake. For example, in FIG. 7 there is illustrated the localization of a suspected tumor much closer to the kidney than in the example described with reference to FIG. 4. In this latter example 600 characteristic x-rays are detected, while 42560 full energy gamma-rays are detected. The ratio of characteristic x-rays to gamma-rays in this case being disproportionately small indicates to the surgeon that there is an intense deep source of uptake in the probe's field of view, from which only gamma rays are detected, as well as a closer source of radiation from which x-rays are detected. Thus, the surgeon should continue the search in a similar manner to that described earlier. In particular, moving the probe to the left as illustrated in FIG. 8 until the numbers of detected x-rays drop to 30, while the number of detected gamma-rays drop to 32240 indicates that the suspected tumor is no longer within the probe's field of view, but that a deep source of uptake still is. By orienting the probe similarly to that shown in FIG. 6 and by narrowing the probe's field of view as shown in FIG. 9 by using the collimator 22E on the probe 22, the surgeon is able to detect 300 characteristic x-rays and 9450 full energy gamma-rays, whereupon the surgeon is justified in believing that there probably is no other source of non-specific uptake in the probe's field of view. He or she can further substantiate the location of the suspected tumor by keeping the probe at the same orientation and observing the displays as the probe is moved in different directions along the exposed tissue plane. Thus, the suspected tumor is localized.

Figure 10:
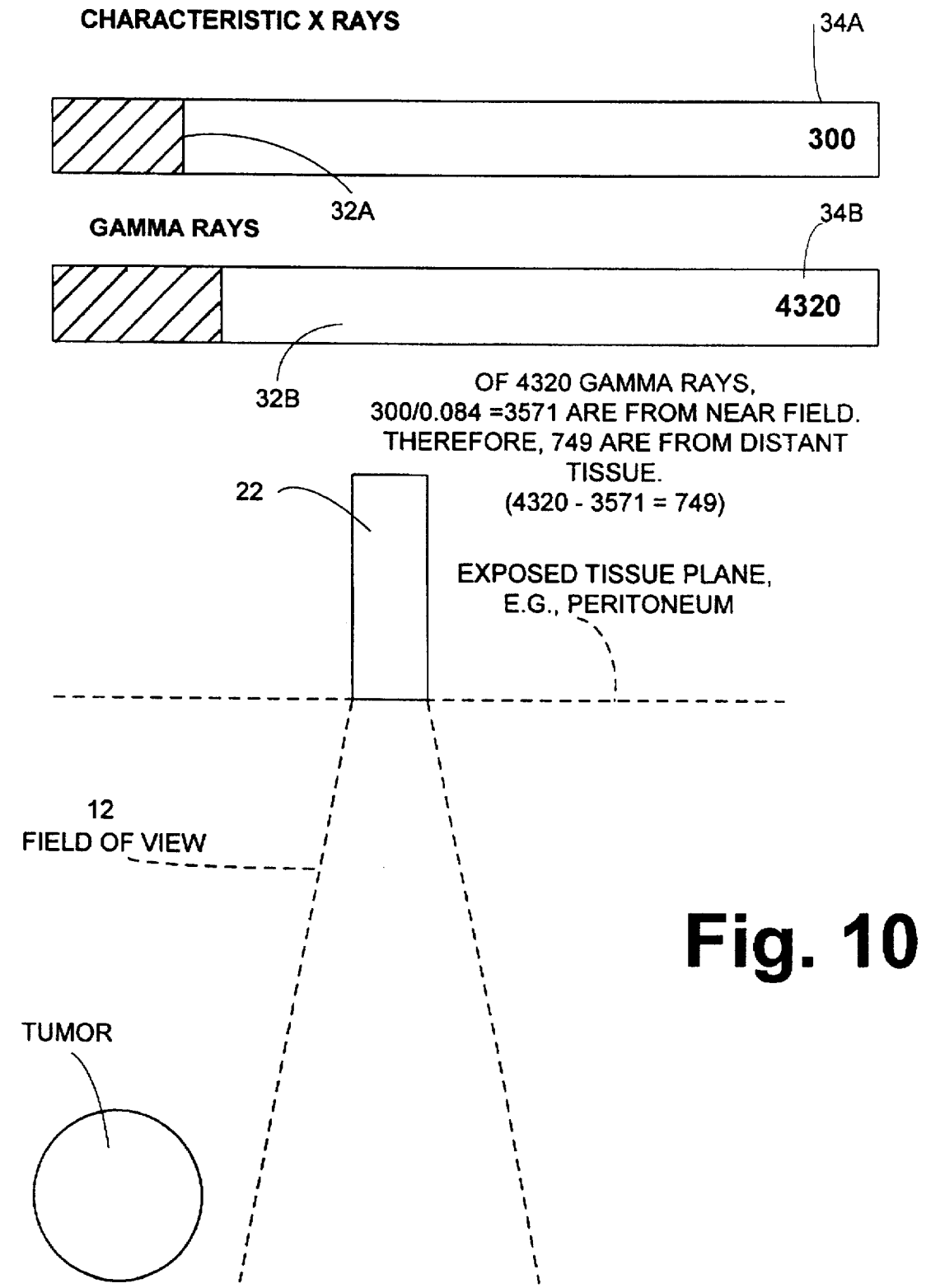
FIG. 10 is an illustration, like that of FIG. 3, but showing a portion of the system shown in FIGS. 1 and 2 being used to determine the location of a radiolabelled tumor located deep within the abdomen in accordance with one aspect of the method of this invention.
Figure 11:
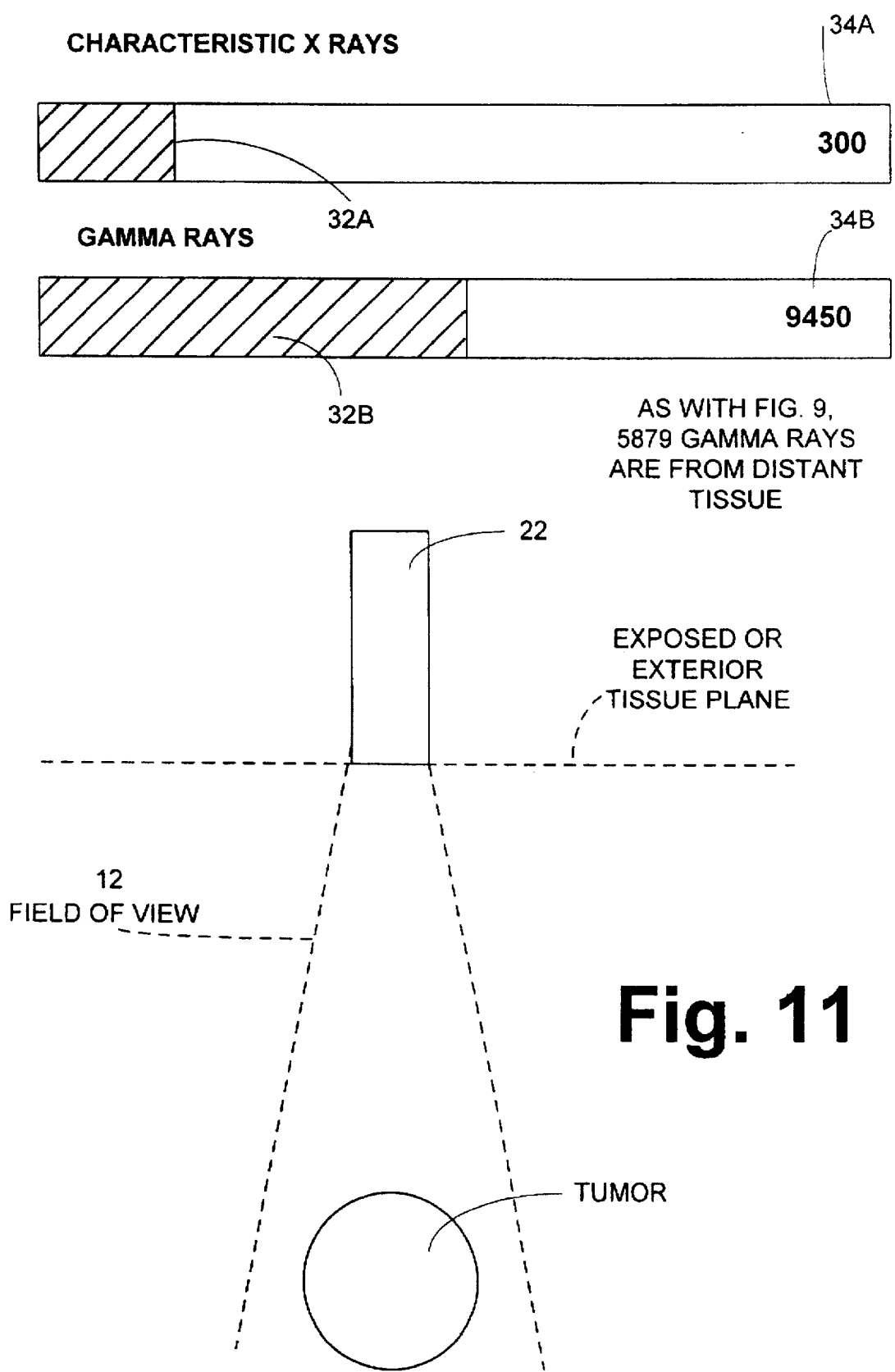
FIG. 11 is an illustration, like that of FIG. 7, but showing the system being used in a later step in determining the location of the radiolabelled tumor of FIG. 10.

In order to localize a specific uptake source, e.g., a suspected tumor, located beyond the near-field for the specific radioisotope used, the system 22 makes use of the detected full energy gamma rays. However, the characteristic x-rays received are also utilized to determine if the ratio of characteristic x-rays to the full energy gamma-rays is appropriate so that the numbers of detected gamma-rays can be used to indicate a distant source of specific uptake. In FIGS. 10 and 11 there is illustrated a process of localizing a Technetium 99 m tagged suspected tumor site located deep within the abdomen of an obese person, and assuming that it is desired not to penetrate the peritoneum tissue plane with the probe 22 to localize the suspected tumor. Thus, in this case the suspected tumor will be beyond the near-field.

In FIG. 10 the probe is illustrated as being off axis of the suspected tumor, with the system detecting 300 characteristic x-rays and 4320 full energy gamma-rays. The light bars 32A and 32B in this case will not be of equal length since the ratio of characteristic x-rays to full energy gamma-rays will be disproportionately low. In addition, when the surgeon moves the probe to locations adjacent to that shown in FIG. 10 in any direction other than that which moves it over the suspected tumor, the relative numbers of detected gamma rays and characteristic x rays will not appreciably change. Thus, the surgeon is justified in believing that the detected radiation probably represents background radiation from low concentration uptake generally present throughout the tissue, and further searching must be conducted to localize the tumor. To achieve that end the probe is moved in either the x or y direction (left/right or up/down, respectively). In the illustration of FIG. 11 the probe is shown having been moved in the x direction to the left until the numbers of detected gamma rays increase. In this example the numbers of detected characteristic x-rays remain at 300, since the source of x rays remains the tissue close to the probe, with the low concentration of uptake. However, the numbers of detected gamma-rays increase to 9450 when the probe is on axis (i.e., centered) with the suspected tumor, and then decrease as the probe is moved in any direction away from the suspected tumor such that the suspected tumor is again out of the field of view of the probe. Since the radiotracer being used has been tagged with Technetium 99 m, for a reading of 300 characteristic x-rays there would be an associated 3571 full energy gamma-rays, if there were no tissue intervening between the site of uptake and the radiation-detecting probe. Therefore, from the readings received the surgeon is justified in believing that 5879 gamma-rays (9450−3571) are probably coming from deeper, far-field sources of uptake, which the surgeon may know from anatomical knowledge to include a possible tumor, located beyond the near-field. Moreover, from the gamma-ray reading when the probe was off axis (FIG. 10) the surgeon is able to determine that of the 4320 gamma rays detected, 749 (4320−3571) probably represent other deeper, far-field sources of uptake, which could represent background from non-specific uptake such as that in blood pool, extracellular fluid, etc., from within the field of view of the probe.

If one were only to examine the numbers of detected gamma rays of FIGS. 10 and 11, as has characterized the prior art, and not separately take into account the numbers of detected characteristic x-rays and their ratios to the numbers of detected gamma rays, the ratio of suspected distant tumor gamma rays detected (the numbers of detected gamma rays of FIG. 11 when the probe is "on axis") to the background radiation detected (the numbers of detected gamma rays of FIG. 10 when the probe is "off axis") is 9450/4320. Thus, using the prior art examination of only gamma-rays results in a suspected tumor-to-background ratio of 2.19. However, using the system 20, the ratio of distant far-field gamma rays detected to the background gamma rays detected is 2879/749 or 7.85. This significantly higher tumor-to-background or contrast ratio provides the surgeon with a much better confidence level that the suspected tumor has, in fact, been localized.

Figure 15:
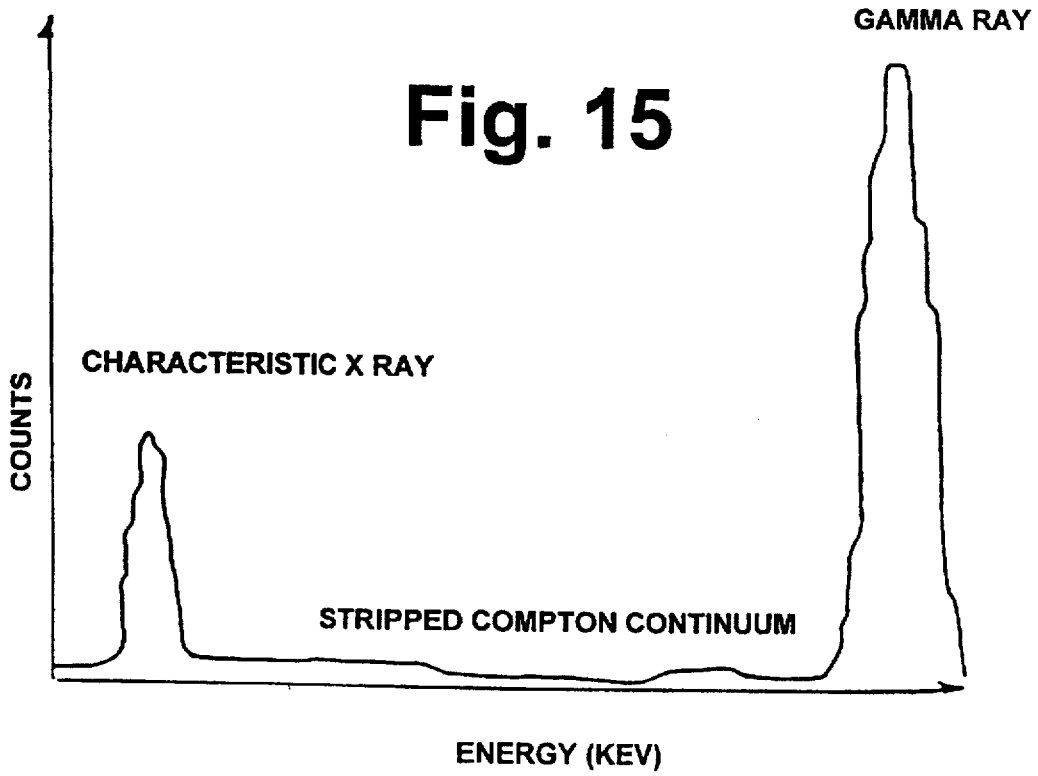
FIG. 15 is a histogram, like FIG. 14, but showing the spectrum of radiation counts obtained by the system of FIG. 1 during the localization of the tumor in accordance with another and option aspect of this invention to remove the effects of Compton scatter in the measured readings of radiation detected.

As mentioned earlier, in many instances it is desirable that the numbers displayed represent the characteristic x rays and full energy gamma rays, but not any received Compton-scattered photons. This can be partially achieved by utilizing the collimator 22E on the probe 22 to minimize the number of Compton-scattered photons received. The goal may be more fully achieved by the characteristic x-ray isolation means 30L and the gamma-ray isolation means described earlier for substantially stripping or removing the signal representing the Compton continuum from the signal representing the spectrum of all photons received, to provide a processed signal representing primarily the characteristic x rays received and the full energy gamma rays received as shown in FIG. 15.

It must be reiterated at this juncture that while the removal of the signal representing Compton-scattered photons from the counts received is desirable, it is not mandatory. Thus, the system 20 need not remove data on Compton-scattered photons in order to enable the precise localization of specific uptake tissue.

It should be appreciated by those skilled in the art that the relative surface X, Y location and depth Z Cartesian coordinates of suspected tumor tissue established by this invention can be compared visually to gamma camera planar and three dimensional images. As a further refinement, absolute X, Y location and depth Z Cartesian coordinates of suspected tumor tissue established by this system can be correlated by computer with the corresponding absolute X, Y location and depth Z Cartesian coordinates of three dimensional gamma camera images previously obtained. Thus, a virtual map of the three dimensional distribution of suspected tumor tissue relative to probe position and angular orientation (taking into account the probe's distance from the external tissue plane) can be tracked with feedback signals from appropriate commercially available x, y, z and angular orientation position sensing apparatus (not shown), attached to the surgical probe.

In summary, the subject invention can utilize only the detection of short range, e.g., approximately 15-30 keV, characteristic x-rays as a signal in itself to guide the practitioner in orienting the probe to a site of near-field specific uptake. In addition, the detected characteristic x-ray signal, when compared to the associated full-energy gamma-ray signal, can also serve as an indication of the depth of origin of the detected gamma rays. When no angular orientation of the probe can provide substantially pure near-field signal of full energy gamma rays, the near-field signal alone can be electronically selected by using only the low energy characteristic x-ray signal. When, on the other hand, angular orientation of the probe indicates a high ratio of the number of detected characteristic x-rays to the number of detected gamma rays, demonstrating substantial near-field origin of the majority of the stronger gamma rays, then the number of detected gamma rays is accepted as indicating nearby uptake, i.e., radiolabelled tissue. When radioisotopes such as Technetium 99 m are in use, wherein characteristic x-rays are much less abundant than full energy gamma rays it may be preferable to use the much stronger signal, with greater directional information, provided by the full-energy gamma rays.

For suspected tumors deeper within the tissue or within the "far-field", the practitioner using the system of this invention can electronically select only those detected gamma rays which originate from the far field, in order to localize the site of uptake.

In addition, as previously described, the system of this invention allows measurements of the line shape of detected full-energy gamma ray peaks to provide information on the depth of sites of uptake.

Thus, the subject invention provides the practitioner with the choice of whichever signal provides the greatest information according to the specific surgical or diagnostic problem.

Lastly, it should be pointed out that while the subject invention has been discussed with reference to detection of radioactively tagged tissue, it can be used for other purposes as well, e.g., non-destructive testing of materials and structures.

Without further elaboration, the foregoing will so fully illustrate our invention that others may, by applying current or future knowledge, adopt the same for use under various conditions of service.

What is claimed is:

1. A system for determining the location of a mass of radiolabelled tissue with respect to a reference point, the tissue having been provided with at least one radiolabelled tracer producing gamma-ray photons, characteristic x-ray photons, and an associated continuum of Compton-scattered photons, said system comprising radiation detecting means, signal processing means and signal analyzing means, said radiation detecting means being positionable to a location adjacent the radiolabelled tissue for detecting the photons emitted thereby and for providing an electrical signal representative of the received photons, said radiation detecting means and its position relative to the tissue establishing the reference point, said signal processing means utilizing said electrical signal to produce a processed electrical signal being representative of the number of photons detected as a function of their energies, said analyzing means being arranged for analyzing portions of said processed signal utilizing the known naturally occurring abundance of emitted photons of different energies represented by said processed signal for said at least one radiolabelled tracer as a reference factor in such analysis, whereupon said analysis of portions of said processed signal utilizing said reference factor establishes the location of the mass of radiolabelled tissue with respect to the reference point.

2. The system of claim 1 wherein said system includes first means to ensure that only minimal portions of said processed signal represent Compton scattered photons.

3. The system of claim 2 wherein said signal processing means includes said first means, and wherein said first means is arranged to substantially remove from said electrical signal portions which represent the Compton scattered photons received by said detecting means.

4. The system of claim 2 wherein said detecting means has a field of view for the detection of the photons and includes said first means, said first means comprising collimation means to restrict said field of view of said detecting means, to thereby reduce the number of Compton scattered photons and virtually eliminate x-ray photons and gamma-ray photons received by said detecting means from origins outside said field of view.

5. The system of claim 2 wherein said signal analyzing means comprises window setting means to establish at least one range of photon energy encompassing at least a portion of a selected one of portions of said processed signal representing characteristic x-ray photons received and gamma-ray photons received, while excluding other portion of said processed signal.

6. The system of claim 5 wherein said window setting means establishes a range of photon energy encompassing at least a portion of said processed signal representing characteristic x-ray photons received.

7. The system of claim 5 wherein said window setting means establishes a range of photon energy encompassing at least a portion of said processed signal representing gamma-ray photons received.

8. The system of claim 5 wherein said window setting means establishes a first range of photon energy and a second range of photon energy, said first range encompassing at least a portion of said processed signal representing characteristic x-ray photons received, and said second range encompassing at least a portion of said processed signal representing gamma-ray photons received.

9. The system of claim 8 wherein said window setting means is selectable to select one of said first range, said second range, and said first and second ranges.

10. The system of claim 1 wherein said signal analyzing means comprises window setting means to establish at least one range of photon energy encompassing at least a portion of a selected one of said portions of said processed signal, while excluding other portions of said processed signal.

11. The system of claim 10 wherein said window setting means establishes a range of photon energy encompassing at least a portion of said processed signal representing characteristic x-ray photons received.

12. The system of claim 10 wherein said window setting means establishes a range of photon energy encompassing at least a portion of said processed signal representing gamma-ray photons received.

13. The system of claim 10 wherein said window setting means establishes a first range of photon energy and a second range of photon energy, said first range encompassing at least a portion of said processed signal representing characteristic x-ray photons received, and said second range encompassing at least a portion of said processed signal representing gamma-ray photons received.

14. The system of claim 13 wherein said window setting means is selectable to select one of said first range, said second range, and said first and second ranges.

15. The system of claim 10 wherein said signal analyzing means comprises peak identification means, and wherein said processed signal is provided to said peak identification means, said peak identification mean being arranged to provide a predetermined reference characteristic x-ray peak signal and a predetermined reference gamma-ray peak signal, to compare said portion of said processed signal representing characteristic x-ray photons received to said predetermined reference characteristic x-ray peak signal.

16. The system of claim 10 wherein said signal analyzing means comprises peak identification means, and wherein said processed signal is provided to said peak identification means, said peak identification means being arranged to provide a predetermined reference characteristic x-ray peak signal and a predetermined reference gamma-ray peak signal and to compare said portion of said processed signal representing characteristic x-ray photons received to said predetermined reference characteristic x-ray peak signal and compare said portion of said processed signal representing gamma-ray photons received to said predetermined reference gamma-ray peak signal.

17. The system of claim 10 wherein said signal analyzing means comprises peak identification means, and wherein said processed signal is provided to said peak identification means, said peak identification means being arranged to provide a predetermined reference gamma-ray peak signal and to compare said portion of said processed signal representing gamma-ray photons received to said predetermined reference gamma-ray peak signal.

18. The system of claim 10 wherein said analyzing means comprises a multichannel analyzer having plural bandwidths, each of said bandwidths defining a respective one of said range of photon energy encompassing at least a portion of a selected one of said portions of said processed signal representing characteristic x-ray photons received and gamma-ray photons received.

19. The system of claim 18 wherein each of said bandwidths is approximately 1 kev.

20. The system of claim 1 wherein said signal analyzing means comprises ratio calculation means, and wherein said processed electrical signal is provided to said ratio calculation means, said ratio calculation means being arranged to utilize plural predetermined reference ratios, each of said reference ratios being a ratio of the gamma-ray photons emitted and the characteristic x-ray photons emitted from at least one radiolabelled tracer after passing a predetermined distance through a predetermined type of tissue, said ratio calculation means utilizing said processed signal to provide a calculated ratio representing the ratio of the number of characteristic x-ray photons making up said portion of said processed signal representing characteristic x-ray photons received to the number of gamma-ray photons making up said portion of said processed signal representing gamma-ray photons received, and comparing said calculated ratio to at least one of said predetermined reference ratios.

21. The system of claim 20 wherein said signal analyzing means comprises subtraction calculation means for subtracting the gamma-ray photons corresponding to the characteristic x-ray photons of said portion of said processed signal representing characteristic x-ray photons received from the total gamma-ray photons of said portion of said processed signal representing gamma-ray photons received.

22. The system of claim 1 wherein said signal analyzing means comprises spectral line shape analyzing means for analyzing the shape of at least a selected one of said portions of said processed signal representing characteristic x-ray photons received and gamma-ray photons received.

23. The system of claim 22 wherein said spectral line shape analyzing means determines the degree of asymmetry of at least a selected one of said portions of said processed signal representing characteristic x-ray photons received and gamma-ray photons received.

24. The system of claim 22 wherein said spectral line shape analyzing means utilizes plural reference shapes, at least one of said reference shapes representing at least a selected one of said portions of said processed signal representing characteristic x-ray photons received and gamma-ray photons received resulting from at least one radiolabelled tracer after passing a predetermined distance through a predetermined type of tissue, said spectral line shape analyzing means comparing the shape of the at least one portion of said processed signal to at least one of said plural reference shapes.

25. The system of claim 22 wherein said spectral line shape analyzing means utilizes plural reference shapes, at least one of said reference shapes representing the gamma-ray portion of said processed signal resulting from at least one radiolabelled tracer after passing a predetermined distance through a predetermined type of tissue, and at least another of said reference shapes representing the characteristic x-ray portion of said processed signal resulting from at least one radiolabelled tracer after passing a predetermined distance through a predetermined type of tissue, said spectral line shape analyzing means comparing the shape of the at least one portion of said processed signal to at least one of said plural reference shapes.

26. The system of claim 1 wherein said radiation detecting means is arranged to be disposed adjacent an exposed or exterior tissue plane and wherein said signal analyzing means comprises spectral line shape analyzing means for analyzing the shape of at least a selected one of said portions of said processed signal representing characteristic x-ray photons received and gamma-ray photons received to provide an indication of the depth of the radiolabelled tissue beneath the exposed or exterior tissue plane.

27. The system of claim 26 wherein said spectral line shape analyzing means determines the degree of asymmetry of at least a selected one of said portions of said processed signal representing characteristic x-ray photons received and gamma-ray photons received to provide an indication of the depth of the radiolabelled tissue beneath the exposed or exterior tissue plane.

28. The system of claim 26 wherein said spectral line shape analyzing means utilizes plural reference shapes, one of said reference shapes representing at least a selected one of said portions of said processed signal representing characteristic x-ray photons received and gamma-ray photons received resulting from at least one radiolabelled tracer after passing a predetermined distance through a predetermined type of tissue, said spectral line shape analyzing means comparing the shape of the at least one portion of said processed signal to at least one of said plural reference shapes to provide an indication of the depth of the radiolabelled tissue beneath the exposed or exterior tissue plane.

29. The system of claim 26 wherein said spectral line shape analyzing means utilizes plural reference shapes, at least one of said reference shapes representing the gamma-ray portion of said processed signal resulting from at least one radiolabelled tracer after passing a predetermined distance through a predetermined type of tissue, and at least another of said reference shapes representing the characteristic x-ray portion of said processed signal resulting from at least one radiolabelled tracer after passing a predetermined distance through a predetermined type of tissue, said spectral line shape analyzing means comparing the shape of the at least one portion of said processed signal to at least one of said plural reference shapes to provide an indication of the depth of the radiolabelled tissue beneath the exposed or exterior tissue plane.

30. The system of claim 1 wherein said radiation detection means has a field of view and is arranged to be oriented at various orientations with respect to the tissue so that said processed electrical signal can be analyzed at each of said orientations and fields of view of said device.

31. The system of claim 30 wherein said radiation detecting means comprises a nuclear uptake probe.

32. The system of claim 31 wherein said probe is hand-holdable.

33. The system of claim 1 wherein said signal analyzing means comprises audible intensity determination means, and wherein said processed electrical signal is provided to said audible intensity determination means, said audible intensity determination means being arranged to emit audible signals representative of the rate at which said characteristic x-ray photons are detected by said radiation detection means.

34. The system of claim 1 wherein said signal analyzing means comprises audible intensity determination means, and wherein said processed electrical signal is provided to said audible intensity determination means, said audible intensity determination means being arranged to emit audible signals representative of the rate at which said gamma-ray photons are detected by said radiation detection means.

35. The system of claim 1 wherein said signal analyzing means comprises audible intensity determination means, and wherein said processed electrical signal is provided to said audible intensity determination means, said audible intensity determination means being arranged to emit first audible signals representative of the rate at which said characteristic x-ray photons are detected by said radiation detection means and to emit second audible signals representative of the rate at which said gamma-ray photons are detected by said radiation detection means.

36. The system of claim 1 wherein said signal analyzing means comprises signaling means to provide at least one signal representative of the ratio of the characteristic x-ray photons received to the gamma ray photons received, said signal indicating when said ratio is appropriate for the natural abundance of said photons of the radiolabelled tracer.

37. The system of claim 36 wherein said signaling means produces a pair of visible graphic displays, one for said characteristic x-ray photons received, and the other for said gamma ray photons received.

38. The system of claim 37 further comprises means for normalizing wherein said graphic displays to the ratio of the naturally occurring abundance of characteristic x-ray photons and gamma ray photons of the radiolabelled tracer.

39. The system of claim 36 wherein said signaling means produces a pair of audible signals, one for said characteristic x-ray photons received, and the other for said gamma ray photons received.

40. The system of claim 39 further comprises means for normalizing said audible signals to for the ratio of the naturally occurring abundance of characteristic x-ray photons and gamma ray photons of the radiolabelled tracer.

41. A method for determining the location of a mass of radiolabelled tissue with respect to a reference point comprising:
  a) providing the tissue with at least one radiolabelled tracer that produces gamma-ray photons, characteristic x-ray photons, and an associated continuum of Compton scattered photons;
  b) providing radiation detecting means adjacent the tissue, detecting the photons therefrom, and for providing an electrical signal representative of the received photons;
  c) utilizing said radiation detecting means to establish said reference point;
  d) processing said electrical signal to produce a processed electrical signal representative of the number of photons detected as a function of their energies; and
  e) analyzing portions of said processed signal by utilizing the known naturally occurring abundance of emitted photons of different energies represented by said processed signal for said at least one radiolabelled tracer as a reference factor in such analysis, whereupon said analysis of portions of said processed signal utilizing said reference factor establishes the spatial coordinates of the mass of radiolabelled tissue with respect to the reference point.

42. The method of claim 41 additionally comprising the step of ensuring that only minimal portions of said processed signal represent Compton scattered photons.

43. The method of claim 42 additionally comprising the step of substantially removing from said electrical signal portions of said electrical signal which represent the Compton scattered photons received by said detecting means.

44. The method of claim 42 wherein said radiation detecting means has a field of view for detecting the photons, said method additionally comprising the step of restricting said field of view of said detecting means, to thereby reduce the number of Compton scattered photons and gamma-ray photons received by said detecting means from origins outside said field of view.

45. The method of claim 41 additionally comprising the step of establishing at least one range of photon energy encompassing at least a portion of a selected one of said portions of said processed signal representing characteristic x-ray photons received and gamma-ray photons received, while excluding other portions of said processed signal.

46. The method of claim 45 wherein said range of photon energy encompasses at least a portion of said portion of said processed signal representing characteristic x-ray photons received.

47. The method of claim 45 wherein said range of photon energy encompasses at least a portion of said portion of said processed signal representing gamma-ray photons received.

48. The method of claim 45 wherein a first and a second range of photon energy are established, and wherein said first range encompasses at least a portion of said portion of said processed signal representing characteristic x-ray photons received, and said second range encompasses at least a portion of said portion of said processed signal representing gamma-ray photons received.

49. The method of claim 48 wherein said method comprises selecting either said first range, or said second range, or said first and second ranges.

50. The method of claim 45 additionally comprising the steps of:
 f) providing a predetermined reference characteristic x-ray peak signal; and
 g) comparing said portion of said processed signal representing characteristic x-ray photons received to said predetermined reference characteristic x-ray peak signal.

51. The method of claim 45 additionally comprising the steps of:
 f) providing a predetermined reference characteristic x-ray peak signal and predetermined reference gamma-ray peak signal; and
 g) comparing said portion of said processed signal representing characteristic x-ray photons received to said predetermined reference characteristic x-ray peak signal, and comparing said portion of said processed signal representing gamma-ray photons received to said predetermined reference gamma-ray peak signal.

52. The method of claim 45 additionally comprising the steps of:
 f) providing a predetermined reference gamma-ray peak signal; and
 g) comparing said portion of said processed signal representing gamma-ray photons received to said predetermined reference gamma-ray peak signal.

53. The method of claim 41 additionally comprising the steps of:
 f) providing plural predetermined reference ratios, each of said ratios being the ratio of the gamma-ray photons emitted and the characteristic x-ray photons from at least one radiolabelled tracer after passing a predetermined distance through a predetermined type of tissue; and
 g) utilizing said processed electrical signal to provide a calculated ratio representing the ratio of the number of characteristic x-ray photons making up said portion of said processed signal representing characteristic x-ray photons received to the number of gamma-ray photons making up said portion of said processed signal representing gamma-ray photons received; and
 h) comparing said calculated ratio to at least one of said predetermined reference ratios.

54. The method of claim 53 additionally comprising the step of subtracting the gamma-ray photons corresponding to the characteristic x-ray photons of the portion of said processed signal representing characteristic x-ray photons received from the total gamma-ray photons of the portion of said processed signal representing gamma-ray photons received.

55. The method of claim 41 additionally comprising the step of analyzing a shape of at least one portion of said processed signal to provide an indication of the depth of the radiolabelled tissue beneath the exposed or exterior tissue plane.

56. The method of claim 55 wherein said step of analyzing the shape of at least one portion of said processed signal is accomplished by determining the degree of asymmetry of the at least one portion of said processed signal to provide the indication of the depth of the radiolabelled tissue beneath the exposed or exterior tissue plane.

57. The method of claim 56 wherein plural reference shapes are utilized, with at least one of said reference shapes representing at least a selected one of said portions of said processed signal representing characteristic x-ray photons received and gamma-ray photons received resulting from said at least one radiolabelled tracer after passing a predetermined distance through a predetermined type of tissue, and wherein the shape of the at least one portion of said processed signal is compared to at least one of said plural reference shapes.

58. The method of claim 56 wherein plural reference shapes are utilized, with at least one of said reference shapes representing the gamma-ray portion of said processed signal resulting from the least one radiolabelled tracer after passing a predetermined distance through a predetermine type of tissue, and at least another of said reference shapes representing the characteristic x-ray portion of said processed signal resulting from the least one radiolabelled tracer after passing a predetermined distance through a predetermined type of tissue, and wherein the shape of the at least one portion of said processed signal is compared to at least one of said plural reference shapes.

59. The method of claim 41 wherein said radiation detection means has a field of view, and wherein said method comprises the step of orienting said radiation detecting means at various orientations with respect to the tissue so that said processed electrical signal can be analyzed at each of said orientations and fields of view of said device.

60. The method of claim 59 wherein said radiation detecting means comprises a nuclear uptake probe, and further including the step of orientating said probe is accomplished by hand.

61. The method of claim 41 additionally comprising the step of emitting audible signals representative of the rate at which said characteristic x-ray photons are detected by said radiation detection means.

62. The method of claim 41 additionally comprising the step of emitting audible signals representative of the rate at which the gamma-ray photons are detected by said radiation detection means.

63. The method of claim 41 additionally comprising the steps of:
 f) emitting first audible signals representative of the rate at which the characteristic x-ray photons are detected by said radiation detection means; and
 g) emitting second audible signals representative of the rate at which the gamma-ray photons are detected by said radiation detection means.

64. The method of claim 41 wherein said tissue is located within the body of a living being.

65. The method of claim 41 wherein said tissue has been removed from the body of a living being.

66. The method of claim 41 additionally comprising the steps of providing at least one signal representative of the ratio of the characteristic x-ray photons received to the gamma ray photons received, said signal indicating when said ratio is appropriate for the natural abundance of said photons of the radiolabelled tracer.

67. The method of claim 66 wherein said at least one signal comprises a pair of visible graphic displays, one for said characteristic x-ray photons received, and the other for said gamma ray photons received.

68. The method of claim 67 wherein said graphic displays are normalized for the ratio of the naturally occurring abundance of characteristic x-ray photons and gamma ray photons of the radiolabelled tracer.

69. The method of claim 66 wherein said at least one signal comprises a pair of audible signals, one for said characteristic x-ray photons received and the other for said gamma ray photons received.

70. The method of claim 69 wherein said audible signals are normalized for the ratio of the naturally occurring abundance of characteristic x-ray photons and gamma ray photons of the radiolabelled tracer.

71. A system for the localization of a radiation detecting device used in nuclear medicine applications with tissue having been provided with at least one radiolabelled tracer producing gamma-ray photons, characteristic x-ray photons, and an associated continuum of Compton scattered photons, said system comprising a radiation detecting device and processing means, said radiation detecting device for receiving said gamma-ray photons characteristic x-ray photons, and Compton scattered photons and providing an electrical signal representative of the photons received thereby, said processing means being coupled to said radiation detecting means and arranged to establish a narrow energy window of no more than approximately 10 keV and no less than approximately 1 keV centered on the peak of the characteristic x-ray photons produced by the at least one radiolabelled tracer and excluding the peak of the gamma ray photons for providing an output signal representative of the photons received by said radiation detecting device within said narrow energy window.

72. The system of claim 71 wherein only said system is used for the localization of said radiation detecting device, and wherein said device comprises a surgical probe.

73. The system of claim 71 wherein only said system is used for the localization of said radiation detecting device, and wherein said device comprises a gamma-camera.

74. The system of claim 71 wherein only said system is used for the localization of said radiation detecting device, and wherein said device comprises a percutaneous biopsy probe.

75. The system of claim 71 wherein only said system is used for the localization of said radiation detecting device, and wherein said device comprises an endoscopic probe.

76. The system of claim 71 including means for minimizing the representation of the Compton scattered photons within said narrow energy window.

77. The system of claim 71 wherein said output signal is also representative of gamma-ray photons received by said radiation detecting device, and wherein said system additionally comprises signaling means to provide at least one signal representative of a ratio of the characteristic x-ray photons received to the gamma ray photons received, said signal indicating when said ratio is representative of the natural abundance of said photons of the radiolabelled tracer.

78. The system of claim 77 wherein said signaling means produces a pair of visible graphic displays, one for said characteristic x-ray photons and the other for said gamma ray photons.

79. The system of claim 78 wherein further comprises means for normalizing said graphic displays to the ratio of the naturally occurring abundance of characteristic x-ray photons and gamma ray photons of the radiolabelled tracer.

80. The system of claim 77 wherein said signaling means produces a pair of audible signals, one for said characteristic x-ray photons and the other for said gamma ray photons.

81. The system of claim 80 further comprises means for normalizing said audible signals to the ratio of the naturally occurring abundance of characteristic x-ray photons and gamma ray photons of the radiolabelled tracer.

82. A method of positioning a radiation detecting device in a nuclear medicine application involving tissue having been provided with at least one radiolabelled tracer producing gamma-ray photons, characteristic x-ray photons, and an associated continuum of Compton scattered photons, said method comprising:
(a) positioning a radiation detecting device in proximity with tissue having been provided with the at least one radiolabelled tracer;
(b) receiving said gamma-ray photons, characteristic x-ray photons and Compton scattered photons with said device;
(c) establishing a narrow energy window of no more than approximately 10 keV and no less than approximately 1 keV centered on the peak of the characteristic x-ray photons produced by the at least one radiolabelled tracer and excluding the peak of the gamma ray photons; and
(d) providing an output signal representative of the photons received by said radiation detecting device within said narrow energy window.

83. The method of claim 82 additionally comprising the step of utilizing said output signal for guiding the positioning of said radiation detecting device with respect to the radiolabelled tissue.

84. The method of claim 83 additionally comprising the step of minimizing the representation of the Compton scattered photons within said narrow energy window.

85. The method of claim 83 wherein said positioning of said radiation detecting device aligns said device with the radiolabelled tissue.

86. The method of claim 85 wherein said positioning of said radiation detecting device spaces said device from said tissue by a determinable distance.

87. The method of claim 86 wherein said positioning of said radiation detecting device orients said device with respect to the tissue.

88. The method of claim 82 additionally comprising the step of minimizing the representation of the Compton scattered photons within said narrow energy window.

89. The method of claim 82 wherein said output signal is also representative of gamma-ray photons received by said radiation detecting device, and wherein the method additionally comprising the step of providing at least one signal representative of a ratio of the characteristic x-ray photons received to the gamma ray photons received, said signal indicating when said ratio is representative of the natural abundance of said photons of the radiolabelled tracer.

90. The method of claim 89 wherein said least one signal comprises a pair of visible graphic displays, one for said characteristic x-ray photons received and the other for said gamma ray photons received.

91. The method of claim 90 wherein said graphic displays are normalized for the ratio of the naturally occurring abundance of characteristic x-ray photons and gamma ray photons of the radiolabelled tracer.

92. The method of claim 89 wherein said at least one signal comprises a pair of audible signals, one for said characteristic x-ray photons received, and the other for said gamma ray photons received.

93. The method of claim 92 wherein said audible signals are normalized for the ratio of the naturally occurring abundance of characteristic x-ray photons and gamma ray photons of the radiolabelled tracer.

* * * * *